US007575758B2

(12) United States Patent
King et al.

(10) Patent No.: US 7,575,758 B2
(45) Date of Patent: Aug. 18, 2009

(54) ACARICIDAL COMPOSITIONS AND METHODS OF USE THEREOF

(75) Inventors: Glenn F. King, Simsbury, CT (US); Ashis K. Mukherjee, Assam (IN); Stephen K. Wikel, Unionville, CT (US); Brianna Sollod McFarland, Fenton, MO (US)

(73) Assignee: The University of Connecticut, Farmington, CT (US)

( * ) Notice: Subject to any disclaimer, the term of this patent is extended or adjusted under 35 U.S.C. 154(b) by 13 days.

(21) Appl. No.: 11/520,384

(22) Filed: Sep. 13, 2006

(65) Prior Publication Data

US 2007/0066529 A1 Mar. 22, 2007

Related U.S. Application Data

(60) Provisional application No. 60/717,958, filed on Sep. 16, 2005.

(51) Int. Cl.
*A01N 63/00* (2006.01)
*A61K 38/17* (2006.01)
*C07K 14/435* (2006.01)

(52) U.S. Cl. .......................... 424/405; 514/12; 530/324

(58) Field of Classification Search ................. 424/405; 514/12; 530/324
See application file for complete search history.

(56) References Cited

U.S. PATENT DOCUMENTS

| | | | |
|---|---|---|---|
| 4,757,011 | A | 7/1988 | Chaleff et al. |
| 4,769,061 | A | 9/1988 | Comai |
| 4,879,236 | A | 11/1989 | Smith et al. |
| 4,940,835 | A | 7/1990 | Shah et al. |
| 5,578,625 | A | 11/1996 | Suzuki et al. |
| 5,763,568 | A | 6/1998 | Atkinson et al. |
| 5,959,182 | A | 9/1999 | Atkinson et al. |
| 6,342,499 | B1 | 1/2002 | Black et al. |
| 6,583,264 | B2 | 6/2003 | King et al. |
| 2004/0138423 | A1 | 7/2004 | King et al. |

FOREIGN PATENT DOCUMENTS

WO WO 9315108 A1 * 8/1993

OTHER PUBLICATIONS

Altschul, et al.; "Basic Local Alignment Search Tool"; J. Mol. Biol.; 215; pp. 403-410; 1990.
Altschul, et al.: "Gapped BLAST and PSI-BLAST: A New Generation of Protein Database Search Programs"; Nucleic Acids Research; 25; pp. 3389-3402; 1997.
Drylov Bendtsen, et al.; "Improved Prediction of Signal Peptides: SignalP 3.0"; J. Mol. Biol.; 340; pp. 783-795; 2004.
Foil, et al.; "Factors That Influence the Prevalence of Acaricide Resistance and Tick-Borne Diseases"; Veterinary Parasitology; 125; pp. 163-181; 2004.
George; "Present and Future Technologies for Tick Control"; Annals of the New York Academy of Sciences; 916; pp. 583-588; 2000.
Hyde-DeRuyscher, et al.; "Polyomavirus Early-Late Switch is Not Regulated at the Level of Transcription Initiation and is Associated with Changes in RNA Processing"; Proc. Natl. Acad. Sci. USA; 85; pp. 8993-8997; 1988.
Karlin, et al.; "Methods for Assessing the Statistical Significance of Molecular Sequence Features by Using General Scoring Schemes"; Proc. Natl. Acad. Sci. USA; 87; pp. 2264-2268; 1990.
Mitchell; "Acaricide Resistance—Back to Basics"; Trop. Anim. Health Prod.; 28; pp. 53S-58S; 1996.
Tedford, et al.; "Functional Significance of the Beta-Hairpin in the Insecticidal Neurotoxin Omega-Atracotoxin-Hv1a"; J. Biol. Chem.; 276; pp. 26568-26576; 2001.
Wang, et al.; "Discovery and Characterization of a Family of Insecticidal Neurotoxins with a Rare Vicinal Disulfide Bridge"; Nature Structural Biology; 7; pp. 505-513; 2000.
Wang, et al.; "Discovery and Structure of a Potent and Highly Specific Blocker of Insect Calcium Channels"; J. Biol. Chem.; 43; pp. 40306-40312; 2001.
Witty; "Current Strategies in the Search for Novel Antiparastic Agents"; International Journal for Parasitology; 29; pp. 95-103; 1999.

* cited by examiner

*Primary Examiner*—Delia M. Ramirez
*Assistant Examiner*—Rosanne Kosson
(74) *Attorney, Agent, or Firm*—Thomas A. Wootton; Jonathan P. O'Brien; Honigman

(57) ABSTRACT

A method of controlling acarine pests comprises applying to the locus of the acarine pests, an isolated polypeptide toxin, wherein the polypeptide toxin has acaricidal activity. In one embodiment, the polypeptide toxin comprises three intrachain disulfide bonds and/or is a component of a venom of an Australian funnel web spider of the genus *Atrax* or *Hadronyche*. The polypeptide toxins may be applied to the acarine pests themselves, to the environment of the acarine pests, to the hosts of the acarine pests, or to an animal vector of the acarine pests, for example.

10 Claims, 3 Drawing Sheets

ACARICIDAL COMPOSITIONS AND METHODS OF USE THEREOF

CROSS-REFERENCE TO RELATED APPLICATIONS

This application claims the benefit of U.S. Patent Application Ser. No. 60/717,958, filed Sep. 16, 2005, which is incorporated by reference herein in its entirety.

STATEMENT REGARDING FEDERALLY SPONSORED RESEARCH & DEVELOPMENT

The U.S. Government has certain rights in this invention pursuant to National Science Foundation Grant No. MCB0234638.

BACKGROUND

Ticks and mites are both members of the taxonomic order Acari, within the Class Arachnida, and they are collectively referred to as acarines. They are not related to insects. Numerous acarine species are key pests of wildlife, farm and companion animals, humans, and crops.

Ticks are obligate ectoparasites that infest mammals, birds, reptiles, and amphibians. It has been estimated that about 80% of the world's cattle are infested with ticks, causing economic losses of US $7.5 billion. Many tick species are considered a problem primarily because of their ability to transmit numerous pathogens of significant veterinary and human public health importance. Selected examples of the many tick species of importance for pathogen transmission include, but are not limited to, the dog tick *Rhipicephalus sanguineus*, the lone star tick *Amblyomma americanum*, the bont tick *Amblyomma hebraeum*, the tropical bont tick *Amblyomma variegatum*, the winter tick *Dermacentor albipictus*, the tropical horse tick *Dermacentor nitens*, the American dog tick *Dermacentor variabilis*, the Rocky Mountain wood tick *Dermacentor Andersoni*, the cattle ticks *Boophilus microplus* and *Boophilus annulatus, Ixodes ricinus*, and the deer tick *Ixodes scapularis*. The bacterial (including rickettsial), protozoan, and arboviral pathogens transmitted by ticks are responsible for a wide variety of human and animal diseases including, for example, Lyme disease, tularemia, heartwater (cowdriosis), dermatophilosis, anaplasmosis, theileriosis, encephalitis, babesiosis, and various spotted fever group rickettsial diseases, including Rocky Mountain spotted fever. For some ticks, however, the major concern is not pathogen transmission, but rather secretion of paralytic neurotoxins that can sometimes be fatal to animals and humans; ticks in this category include, but are not limited to, the Australian paralysis tick *Ixodes holocyclus* and the African paralysis tick *Ixodes rubicundis*. Ticks also cause significant losses in the livestock industry due to lesions from bites and occurrence of secondary infections.

There are about 7,000 species of plant-feeding (phytophagous) mites, many of which are pests of timber, fruits, vegetables, forest crops, ornamental plants, and stored grains. The majority of these mites belong to the superfamilies Eriophyoidea (gall, erinose, bud, and rust mites) and the agronomically important Tetranychoidea (spider mites and flat mites). In addition, some mites are endo- or ectoparasitic pests of livestock and companion animals, causing diseases such as mange and scabies, while dust mites produce allergens associated with asthma and other allergic conditions in humans. Mites often rapidly acquire resistance to miticidal agents because of their extremely rapid life cycle (e.g., 1-4 weeks) and ability to deposit large numbers of eggs. Some mites are resistant to virtually all extant pesticidal agents.

Mites and ticks are acarines and are not closely related to insects. Consequently most insecticides are not effective against acarines. Chemicals that are effective against acarines are called acaricides. There are at least two major problems with the few available acaricides that are effective against mites and ticks. First, many species of ticks and mites have developed resistance to various classes of these chemicals. There is already widespread resistance to coumaphos and the pyrethroids, and increasing reports of resistance to amitraz. The macrocyclic lactone endectocides are effective against *Boophilus* but not against multi-host ticks. Second, many acaricides are under intense regulatory scrutiny by the U.S. Environmental Protection Agency and some have already been deregistered (e.g., chlorpyrifos and diazinon). The loss of major classes of acaricides due to resistance development or deregistration, combined with more demanding registration requirements for new acaricides, is likely to decrease the pool of effective chemical acaricides in the near future. Thus, there is an urgent need to isolate new and safe acaricidal compounds.

A number of investigators have recognized spider venoms as a possible source of insect toxins. A class of peptide toxins known as the omega-atracotoxins, disclosed in U.S. Pat. No. 5,763,568, were isolated from Australian funnel-web spiders by screening the venom for "anti-cotton bollworm" activity. One of these compounds, designated omega-ACTX-Hv1a, has been shown to selectively inhibit insect, as opposed to mammalian, voltage-gated calcium channel currents. A second, unrelated family of insect-specific peptidic calcium channel blockers are disclosed as being isolated from the same family of spiders in U.S. Pat. No. 6,583,264. There is, however, no suggestion in either of these references that such peptides are useful in killing pests other than insects.

SUMMARY

The present inventors have discovered polypeptide toxins such as the omega-ACTX-1 and omega-ACTX-2 families have acaricidal activity. The biological activity of a representative mature toxin from each toxin family has been characterized. These two prototypical toxins cause irreversible toxicity when injected into the lone star tick *Amblyomma americanum*. The omega-ACTX-1 toxins are also highly lethal when delivered orally to the tick.

In one embodiment, a method of controlling acarine pests comprising applying to the locus of the acarine pests, an isolated polypeptide toxin, wherein the polypeptide toxin has acaricidal activity.

In another embodiment, a method of inhibiting acarine pest infestation in a farm animal, a companion animal, or an animal vector comprises applying to the locus of the acarine pests, an isolated polypeptide toxin, wherein the polypeptide toxin has acaricidal activity.

Another aspect of the invention is directed to an isolated polypeptide toxin which comprises any one of SEQ ID NO: 9, 12, 15, 18, 21, 24, 27, 30, 33, 36, 39, 42, 45, 48, 51 or 54.

DETAILED DESCRIPTION

Figure 1:
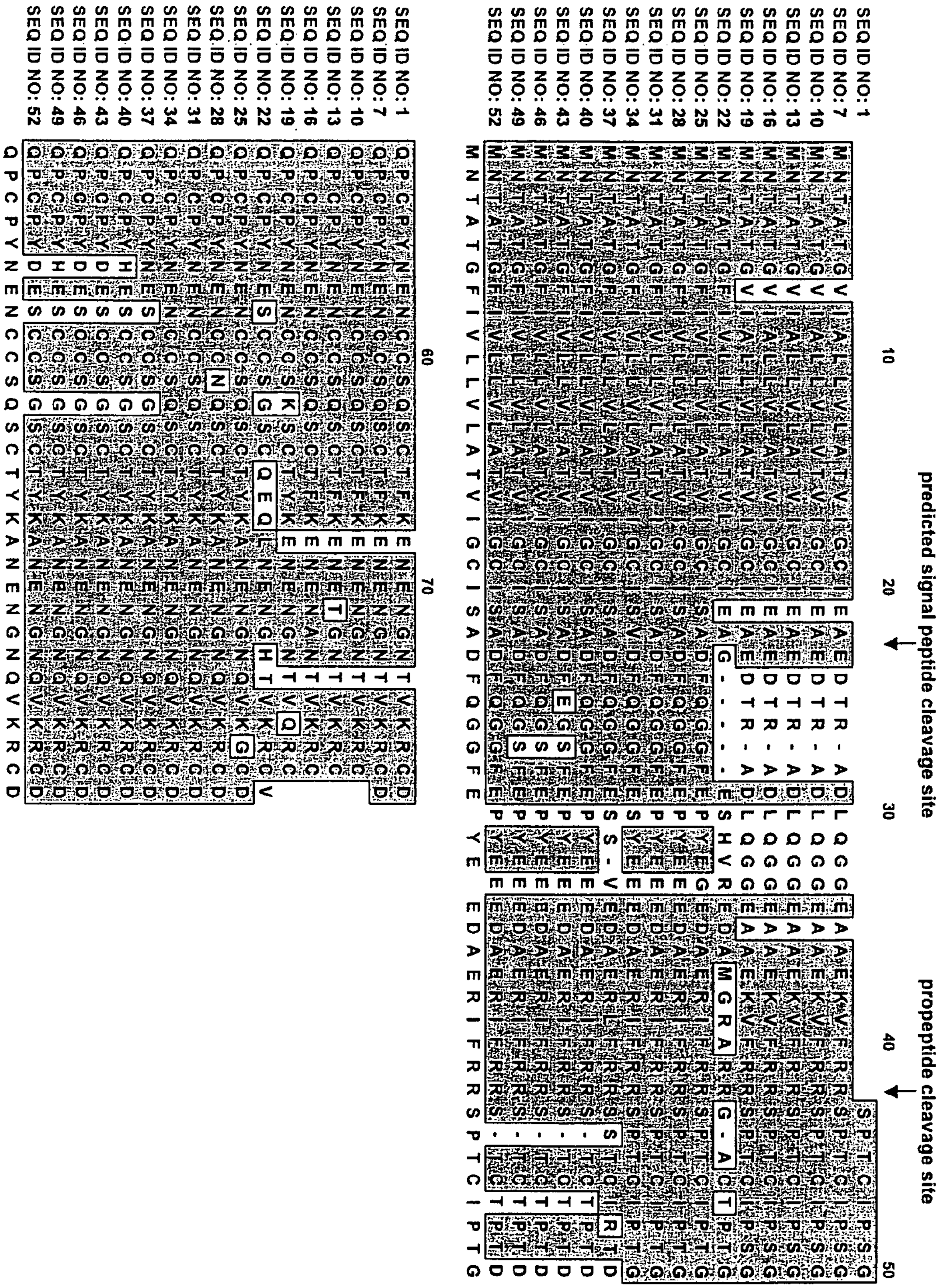
FIG. 1 shows an alignment of omega-ACTX-Hv1a (SEQ ID NO:1) with the complete prepropolypeptide sequences of 16 omega-ACTX-Hv1a orthologs (SEQ ID NOs: 7, 10, 13, 16, 19, 22, 25, 28, 31, 34, 37, 40, 43, 46, 49 or 52). Highly conserved amino acid residues are shaded gray. The vertical arrows indicate the signal peptide and propeptide cleavage sites.

Disclosed herein are methods of controlling acarine pests comprising applying to the locus of the acarine pests an isolated polypeptide toxin, wherein the polypeptide toxin has acaricidal activity. In one embodiment, the polypeptide toxin is a component of a spider venom, such as the venom of an Australian funnel web spider of the genera *Atrax* and *Hadronyche*. Specific polypeptide toxins include the omega-ACTX polypeptide toxins such as the omega-ACTX-1 and omega-ACTX-2 families of polypeptides, as well as the polynucleotides encoding these polypeptides. These polypeptides and the polynucleotides encoding them may be employed as acaricides, either alone or in combination with other acaricidal polypeptides, or genes thereof, or other acaricidal agents. An acaricide or an acaricidal composition is one that is toxic to one or more species of acarine (mites and ticks). Acaricidal activity refers to the ability of polypeptides to kill or paralyze acarines or to inhibit their development or growth. The $LD_{50}$ is the dose of an omega-ACTX polypeptide that results in the death of 50% of the acarines tested.

In one embodiment, the LD50 for a polypeptide toxin such as an omega-ACTX polypeptide dosed to an acarine is less than about 5000 pmol/g, less than about 2500 pmol/g, less than about 1000 pmol/g, less than about 750 pmol/g, less than about 500 pmol/g, or less than about 250 pmol/g, Suitable toxins for use in the disclosed methods are collectively referred to as omega-ACTX polypeptides and include the omega-ACTX-Hv1a (SEQ ID NO:1) and omega-ACTX-Hv2a (SEQ ID NO:2) polypeptides, as well as their homologs.

```
(omega-ACTX-Hv1a):
SPTCIPSGQPCPYNENCCSQSCTFKENENGNTVKRCD    SEQ ID NO:1

(omega-ACTX-Hv2a):
LLACLFGNGRCSSNRDCCELTPVCKRGSCVSSGPGLVGG SEQ ID NO:2
ILGGIL
```

As used herein, an omega-ACTX-Hv1a polypeptide is a polypeptide having a molecular weight of about 4000 Da and a length of about 36 to about 37 amino acids, and that is capable of forming three intrachain disulfide bridges. An omega-ACTX-Hv2a polypeptide is a polypeptide having a molecular weight of about 4500 Da and a length of about 41 to about 45 amino acids, and that is capable of forming three intrachain disulfide bridges. In one embodiment, an omega-ACTX-Hv1a peptide has greater than or equal to 70%, 75%, 80%, 85%, 90% or 95% sequence identity to SEQ ID NO:1 and has insecticidal and/or acaricidal activity. In another embodiment, an omega-ACTX-Hv2a polypeptide has greater than or equal to 70%, 75%, 80%, 85%, 90% or 95% sequence identity to SEQ ID NO:2 and has insecticidal and/or acaricidal activity.

The omega-ACTX polypeptide may be in the form of a mature polypeptide, a prepropolypeptide, or a propolypeptide. Without being held to theory, it is believed that the biologically active form of the omega-ACTX polypeptide is produced by posttranslational proteolytic processing (e.g., cleavage) of the prepropolypeptide precursor to produce the mature polypeptide. Cleavage may be endoproteolytic cleavage of the prepropolypeptide by a protease that recognizes a particular amino acid sequence motif in the prepropolypeptide. The "pre" portion of the prepropolypeptide refers to the signal peptide portion of the prepropolypeptide. Without being held to theory, it is believed that the signal sequence is responsible for targeting the prepropolypeptide to, as well as its translocation across, the endoplasmic reticulum membrane in cells that produce omega-ACTX. In one embodiment, the signal peptide sequence comprises SEQ ID NO: 3 MNTATG$X_1$IALLVLATVIGCI$X_2$A, wherein $X_1$ is V or F and $X_2$ is S or E. Other signal sequences that function in a similar manner may also be employed. In another embodiment, the "pro" part of the prepropolypeptide refers to the sequence SEQ ID NO:4 EDTRADLQGGEAAEKVFRR; SEQ ID NO: 5 DF$X_3$GX4FE$X_5$$X_6$$X_7$$X_8$EDAERIFRR wherein $X_3$ is Q or E, $X_4$ is G or S, $X_5$ is P or S, $X_6$ is Y or S, $X_7$ is E or absent, and $X_8$ is G, E or V; SEQ ID NO:6: GESHVREDAMGRARR, or other sequences covalently attached upstream of a mature omega-ACTX polypeptide. Without being held to theory, possible roles for the pro sequence include facilitating toxin export from the endoplasmic reticulum, assisting enzyme-catalyzed oxidative folding of the mature toxin sequence, and signaling enzymes involved in proteolytic processing and posttranslational modification. The RR motif in the pro sequence is believed to be the endoprotease cleavage site. A purified polypeptide comprising an omega-ACTX polypeptide may thus further comprise a signal peptide sequence (the "pre" sequence, a pro sequence, or a combination thereof.

The signal sequence of about 22 residues (the "pre" sequence) and the propeptide sequence of about 15 residues (the "pro" sequence) are well conserved across the omega-ACTX orthologs. There is typically more variation within the mature toxin sequences than in the signal sequence and the cleavage motif.

In one embodiment, included are the complete preprotein sequences of five orthologs of omega-ACTX-Hv1a (SEQ ID NOs: 7, 10, 13, 16, and 19) which were isolated by analysis of a cDNA library derived from the venom gland of a male Australian funnel-web spider *Atrax robustus:*

In one embodiment, the omega-ACTX-Hv1a ortholog comprises the prepropeptide sequence of SEQ ID NO: 7:

```
SEQ ID NO:7:
MNTATGVIALLVLATVIGCIEAEDTRADLQGGEAAEK

VFRRSPTCIPSGQPCPYNENCCSQSCTFKENENGNTV

KRCD
```

A polynucleotide encoding SEQ ID NO:7 is SEQ ID NO:8:

```
ATGAATACCG CTACAGGTGT CATCGCTCTT   SEQ ID NO:8

TTGGTTCTGG CGACAGTCAT CGGATGCATT

GAAGCAGAAG ATACCAGAGC AGATCTTCAA

GGAGGAGAAG CCGCCGAGAA AGTATTTCGC

CGCTCCCCGA CTTGCATTCC ATCTGGTCAA

CCATGTCCCT ACAACGAAAA TTGCTGCAGC

CAATCGTGTA CATTTAAGGA AAATGAAAAC

GGCAACACTG TTAAAAGATG CGAC
```

The mature polypeptide toxin corresponding to SEQ ID NO:7 is SEQ ID NO:9:

```
SEQ ID NO:9:
SPTCIPSGQPCPYNENCCSQSCTFKENENGNTVKRCD
```

In another embodiment, the omega-ACTX-Hv1a ortholog comprises the prepropeptide sequence of SEQ ID NO:10:

```
SEQ ID NO:10:
MNTATGVIALLVLVTVIGCIEAEDTRADLQGGEAAEK

VFRRSPTCIPSGQPCPYNENCCSQSCTFKENENGNTV

KRCD
```

A polynucleotide encoding SEQ ID NO:10 is SEQ ID NO:11:

```
ATGAATACCG CTACAGGTGT CATCGCTCTT   SEQ ID NO:11

TTGGTTCTGG TGACAGTCAT CGGATGCATT

GAAGCAGAAG ATACCAGAGC AGATCTTCAA

GGAGGAGAAG CCGCCGAGAA AGTATTTCGC

CGCTCCCCGA CTTGCATTCC ATCTGGTCAA

CCATGTCCCT ACAACGAAAA TTGCTGCAGC

CAATCGTGTA CATTTAAGGA AAATGAAAAC

GGCAACACTG TTAAAAGATG CGAC
```

The mature polypeptide toxin corresponding to SEQ ID NO:10 is SEQ ID NO:12:

```
SEQ ID NO:12:
SPTCIPSGQPCPYNENCCSQSCTFKENENGNTVKRCD
```

In another embodiment, the omega-ACTX-Hv1a ortholog comprises the prepropeptide sequence of SEQ ID NO:13:

```
SEQ ID NO:13:
MNTATGVIALLVLATVIGCIEAEDTRADLQGGEAAEK

VFRRSPTCIPSGQPCPYNENCCSQSCTFKENETGNTV

KRCD
```

A polynucleotide encoding SEQ ID NO:13 is SEQ ID NO:14:

```
ATGAATACCG CTACAGGTGT CATCGCTCTT   SEQ ID NO:14

TTGGTTCTGG CGACAGTCAT CGGATGCATT

GAAGCAGAAG ATACCAGAGC AGATCTTCAA

GGAGGAGAAG CCGCCGAGAA AGTATTTCGC

CGCTCCCCGA CTTGCATTCC ATCTGGTCAA

CCATGTCCCT ACAACGAAAA TTGCTGCAGC

CAATCGTGTA CATTTAAGGA AAATGAAACC

GGCAACACTG TTAAAAGATG CGAC
```

The mature polypeptide toxin corresponding to SEQ ID NO:13 is SEQ ID NO:15:

```
SEQ ID NO:15:
SPTCIPSGQPCPYNENCCSQSCTFKENETGNTVKRCD
```

In another embodiment, the omega-ACTX-Hv1a ortholog comprises the prepropeptide sequence of SEQ ID NO:16:

```
                                                  SEQ ID NO:16
MNTATGVIALLVLATVIGCIEAEDTRADLQGGEAAEKVFRRSPTCIPSGQ

PCPYNENCCSQSCTFKENENANTVKRCD
```

A polynucleotide encoding SEQ ID NO:16 is SEQ ID NO:17:

```
SEQ ID NO:17:
ATGAATACCG CTACAGGTGT CATCGCTCTT TTGGTTCTGG

CGACAGTCAT CGGATGCATT GAAGCAGAAG ATACCAGAGC

AGATCTTCAA GGAGGAGAAG CCGCCGAGAA AGTATTTCGC

CGCTCCCCGA CTTGCATTCC ATCTGGTCAA CCATGTCCCT

ACAACGAAAA TTGCTGCAGC CAATCGTGTA CATTTAAGGA

AAATGAAAAC GCCAACACTG TTAAAAGATG CGAC
```

The mature polypeptide toxin corresponding to SEQ ID NO:16 is SEQ ID NO:18:

```
SEQ ID NO:18:
SPTCIPSGQPCPYNENCCSQSCTFKENENANTVKRCD
```

In another embodiment, the omega-ACTX-Hv1a ortholog comprises the prepropeptide sequence of SEQ ID NO:19:

```
                                                  SEQ ID NO:19
MNTATGVIALLVLATVIGCIEAEDTRADLQGGEAAEKVFRRSPTCIPSGQ

PCPYNENCCSKSCTYKENENGNTVQRCD
```

A polynucleotide encoding SEQ ID NO:19 is SEQ ID NO:20:

```
SEQ ID NO:20:
ATGAATACCG CTACAGGTGT CATCGCTCTT TTGGTTCTGG

CGACAGTCAT CGGATGCATT GAAGCAGAAG ATACCAGAGC

AGATCTTCAA GGAGGAGAAG CCGCCGAGAA AGTATTTCGC

CGCTCCCCGA CTTGCATTCC ATCTGGTCAA CCATGTCCCT

ACAACGAAAA TTGCTGCAGC AAATCGTGTA CATATAAGGA

AAATGAAAAT GGCAACACTG TTCAAAGATG CGAC
```

The mature polypeptide toxin corresponding to SEQ ID NO:19 is SEQ ID NO:21:

```
SEQ ID NO:21:
SPTCIPSGQPCPYNENCCSKSCTYKENENGNTVQRCD
```

Also included is the complete preprotein sequence of one ortholog of omega-ACTX-Hv1a (SEQ ID NO:22) which was isolated by analysis of a cDNA library derived from the venom gland of a female Australian funnel-web spider *Atrax robustus*:

```
                                                  SEQ ID NO:22
MNTATGFIVLLVLATVLGCIEAGESHVREDAMGRARRGACTPTGQPCPYN

ESCCSGSCQEQLNENGHTVKRCV
```

A polynucleotide encoding SEQ ID NO:22 is SEQ ID NO:23:

```
SEQ ID NO:23:
ATGAATACCG CAACAGGTTT CATTGTCCTT TTGGTTTTGG
CGACAGTTCT TGGATGCATT GAAGCAGGAG AATCTCATGT
GAGAGAAGAC GCCATGGGAA GAGCTCGCCG GGGGGCTTGC
ACTCCAACTG GTCAACCGTG CCCGTATAAC GAAAGTTGTT
GCAGCGGTTC CTGCCAAGAA CAGCTAAATG AAAACGGACA
CACTGTTAAA AGATGCGTT
```

The mature polypeptide toxin corresponding to SEQ ID NO:22 is SEQ ID NO: 24:

```
SEQ ID NO:24:
GACTPTGQPCPYNESCCSGSCQEQLNENGHTVKRCV
```

Also included are the complete preprotein sequences of ten orthologs of omega-ACTX-Hv1a (SEQ ID NOs: 25, 28, 31, 34, 37, 40, 43, 45, 49, and 52) which were isolated by analysis of a cDNA library derived from the venom gland of a female Australian funnel-web spider *Hadronyche infensa*:

```
                                       SEQ ID NO:25
MNTATGFIVLLVLATVIGCISADFQGGFEPYEGEDAE
RIFRRSPTCIPTGQPCPYNENCCSQSCTYKANENGNQ
VKGCD
```

A polynucleotide encoding SEQ ID NO:25 is SEQ ID NO:26:

```
SEQ ID NO:26:
ATGAATACCG CTACAGGTTT CATCGTACTT TTGGTTTTGG
CGACAGTGAT CGGATGCATT TCTGCAGATT TTCAAGGAGG
TTTCGAACCT TATGAAGGAG AAGACGCCGA AAGAATATTT
CGCCGCTCCC CAACTTGCAT TCCAACTGGT CAACCGTGTC
CCTACAACGA AAATTGCTGC AGCCAATCCT GTACATATAA
GGCAAATGAA AACGGCAACC AAGTTAAAGG ATGCGAC
```

The mature polypeptide toxin corresponding to SEQ ID NO:25 is SEQ ID NO:27:

```
SEQ ID NO:27:
SPTCIPTGQPCPYNENCCSQSCTYKANENGNQVKGCD
```

In one embodiment, the omega-ACTX-Hv1a ortholog comprises the prepropeptide sequence of SEQ ID NO:28.

```
                                       SEQ ID NO:28
MNTATGFIVLLVLATVIGCISADFQGGFEPYEEEDAE
RIFRRSPTCIPTGQPCPYNENCCNQSCTYKANENGNQ
VKRCD
```

A polynucleotide encoding SEQ ID NO:28 is SEQ ID NO:29:

```
SEQ ID NO:29:
ATGAATACCG CTACAGGTTT CATCGTACTT
TTGGTTTTGG CGACAGTGAT CGGATGCATT
TCTGCAGATT TTCAAGGAGG TTTCGAACCT
TATGAAGAAG AAGACGCCGA AAGAATATTT
CGCCGCTCCC CAACTTGCAT TCCAACTGGT
CAACCGTGTC CCTACAACGA AAATTGCTGC
AACCAATCCT GTACATATAA GGCAAATGAA
AACGGCAACC AAGTTAAAAG ATGCGAC
```

The mature polypeptide toxin corresponding to SEQ ID NO:28 is SEQ ID NO:30:

```
SEQ ID NO:30:
SPTCIPTGQPCPYNENCCNQSCTYKANENGNQVKRCD
```

In another embodiment, the omega-ACTX-Hv1a ortholog comprises the prepropeptide sequence of SEQ ID NO:31:

```
                                       SEQ ID NO:31
MNTATGFIVLLVLATVIGCISADFQGGFEPYEEEDAE
RIFRRSPTCIPTGQPCPYNENCCSQSCTYKANENGNQ
VKRCD
```

A polynucleotide encoding SEQ ID NO:31 is SEQ ID NO:32:

```
SEQ ID NO:32:
ATGAATACCG CTACAGGTTT CATCGTACTT
TTGGTTTTGG CGACAGTGAT CGGATGCATT
TCTGCAGATT TTCAAGGAGG TTTCGAACCT
TATGAAGAAG AAGACGCCGA AAGAATATTT
CGCCGCTCCC CAACTTGCAT TCCAACTGGT
CAACCGTGTC CCTACAACGA AAATTGCTGC
AGCCAATCCT GTACATATAA GGCAAATGAA
AACGGCAACC AAGTTAAAAG ATGCGAC
```

The mature polypeptide toxin corresponding to SEQ ID NO:31 is SEQ ID NO:33:

```
SEQ ID NO:33:
SPTCIPTGQPCPYNENCCSQSCTYKANENGNQVKRCD
```

In another embodiment, the omega-ACTX-Hv1a ortholog comprises the prepropeptide sequence of SEQ ID NO:34.

```
                                       SEQ ID NO:34
MNTATGFIVLLVLATVIGCISVDFQGGFESYEEEDAE
RIFRRSPTCIPTGQPCPYNENCCSQSCTYKANENGNQ
VKRCD
```

A polynucleotide encoding SEQ ID NO:34 is SEQ ID NO:35:

```
SEQ ID NO:35:
ATGAATACCG CTACAGGTTT CATCGTACTT

TTGGTTTTGG CGACAGTGAT CGGATGTATT

TCTGTAGATT TTCAAGGAGG TTTCGAATCT

TATGAAGAAG AAGACGCCGA AAGAATATTT

CGCCGCTCCC CAACTTGCAT TCCAACTGGT

CAACCGTGTC CCTACAACGA AAATTGCTGC

AGCCAATCCT GTACATATAA GGCAAATGAA

AACGGCAACC AAGTTAAAAG ATGCGAC
```

The mature polypeptide toxin corresponding to SEQ ID NO:34 is SEQ ID NO: 36:

```
SEQ ID NO:36:
SPTCIPTGQPCPYNENCCSQSCTYKANENGNQVKRCD
```

In another embodiment, the omega-ACTX-Hv1a ortholog comprises the prepropeptide sequence of SEQ ID NO:37:

```
SEQ ID NO:37
MNTATGFIVLLVLATVIGCISADFQGGFESSVEDAERLFRRSSTCIRTDQ

PCPYNESCCSGSCTYKANENGNQVKRCD
```

A polynucleotide encoding SEQ ID NO:37 is SEQ ID NO:38:

```
SEQ ID NO:38:
ATGAATACCG CTACAGGTTT CATCGTTCTT TTGGTTTTGG

CGACAGTGAT CGGATGCATT TCTGCAGATT TTCAAGGAGG

TTTCGAATCT TCTGTAGAAG ACGCCGAAAG ATTATTTCGC

CGCTCCTCAA CTTGCATTCG AACTGATCAA CCGTGCCCCT

ACAACGAAAG TTGCTGCAGC GGTTCCTGTA CATATAAGGC

AAATGAAAAC GGAAACCAAG TTAAAAGATG CGAC
```

The mature polypeptide toxin corresponding to SEQ ID NO:37 is SEQ ID NO:39:

```
SEQ ID NO:39:
SSTCIRTDQPCPYNESCCSGSCTYKANENGNQVKRCD
```

In another embodiment, the omega-ACTX-Hv1a ortholog comprises the prepropeptide sequence of SEQ ID NO:40.

```
SEQ ID NO:40
MNTATGFIVLLVLATVIGCISADFQGGFEPYEEEDAERIFRRSTCTPTDQ

PCPYHESCCSGSCTYKANENGNQVKRCD
```

A polynucleotide encoding SEQ ID NO:40 is SEQ ID NO:41:

```
SEQ ID NO:41:
ATGAATACCG CTACAGGTTT CATCGTACTT TTGGTTTTGG
```

-continued

```
CGACAGTGAT CGGATGCATT TCTGCAGATT TTCAAGGAGG

TTTCGAACCT TATGAAGAAG AAGACGCCGA AAGAATATTT

CGCCGCTCAA CTTGCACTCC AACTGATCAA CCGTGCCCCT

ACCACGAAAG TTGCTGCAGC GGTTCCTGTA CATATAAGGC

AAATGAAAAC GGCAACCAAG TTAAAAGATG CGAC
```

The mature polypeptide toxin corresponding to SEQ ID NO:40 is SEQ ID NO:42:

```
SEQ ID NO:42:
STCTPTDQPCPYHESCCSGSCTYKANENGNQVKRCD
```

In another embodiment, the omega-ACTX-Hv1a ortholog comprises the prepropeptide sequence of SEQ ID NO:43.

```
SEQ ID NO:43
MNTATGFIVLLVLATVIGCISADFEGSFEPYEEEDAERIFRRSTCTPTDQ

PCPYDESCCSGSCTYKANENGNQVKRCD
```

A polynucleotide encoding SEQ ID NO:43 is SEQ ID NO:44:

```
SEQ ID NO:44:
ATGAATACCG CTACAGGTTT CATCGTACTT TTGGTTTTGG

CGACAGTGAT CGGATGCATT TCTGCTGATT TTGAAGGAAG

TTTCGAACCT TATGAAGAAG AAGACGCCGA AAGAATATTT

CGCCGCTCAA CTTGCACTCC AACTGATCAA CCGTGCCCCT

ACGACGAAAG TTGCTGCAGC GGTTCCTGTA CATATAAGGC

AAATGAAAAC GGCAACCAAG TTAAAAGATG CGAC
```

The mature polypeptide toxin corresponding to SEQ ID NO:43 is SEQ ID NO:45:

```
SEQ ID NO:45:
STCTPTDQPCPYDESCCSGSCTYKANENGNQVKRCD
```

In another embodiment, the omega-ACTX-Hv1a ortholog comprises the prepropeptide sequence of SEQ ID NO:46.

```
SEQ ID NO:46:
MNTATGFIVLLVLATVIGCISADFQGSFEPYEEEDAERIFRRSTCTPTDQ

PCPYDESCCSGSCTYKANENGNQVKRCD
```

A polynucleotide encoding SEQ ID NO:46 is SEQ ID NO:47:

```
SEQ ID NO:47:
ATGAATACCG CTACAGGTTT CATCGTTCTT TTGGTTTTGG

CGACAGTGAT CGGATGCATT TCTGCAGATT TTCAAGGAAG

TTTCGAACCT TATGAAGAAG AAGACGCCGA AAGAATATTT

CGCCGCTCAA CTTGCACTCC AACTGATCAA CCGTGCCCCT

ACGACGAAAG TTGCTGCAGC GGTTCCTGTA CATATAAGGC

AAATGAAAAC GGCAACCAAG TTAAAAGATG TGAC
```

The mature polypeptide toxin corresponding to SEQ ID NO:46 is SEQ ID NO:48:

```
SEQ ID NO:48:
STCTPTDQPCPYDESCCSGSCTYKANENGNQVKRCD
```

In another embodiment, the omega-ACTX-Hv1a ortholog comprises the prepropeptide sequence of SEQ ID NO:49:

```
SEQ ID NO:49
MNTATGFIVLLVLATVIGCISADFQGSFEPYEEEDAERIFRRSTCTPTDQ

PCPYHESCCSGSCTYKANENGNQVKRCD
```

A polynucleotide encoding SEQ ID NO:49 is SEQ ID NO:50:

```
SEQ ID NO:50:
ATGAATACCG CTACAGGTTT CATCGTACTT TTGGTTTTGG

CGACAGTGAT CGGATGCATT TCTGCAGATT TTCAAGGAAG

TTTCGAACCT TATGAAGAAG AAGACGCCGA AAGAATATTT

CGCCGCTCAA CTTGCACTCC AACTGATCAA CCGTGCCCCT

ACCACGAAAG TTGCTGCAGC GGTTCCTGTA CATATAAGGC

AAATGAAAAC GGCAACCAAG TTAAAAGATG CGAC
```

The mature polypeptide toxin corresponding to SEQ ID NO:49 is SEQ ID NO:51:

```
SEQ ID NO:51:
STCTPTDQPCPYHESCCSGSCTYKANENGNQVKRCD
```

In another embodiment, the omega-ACTX-Hv1a ortholog comprises the prepropeptide sequence of SEQ ID NO:52:

```
SEQ ID NO:52
MNTATGFIVLLVLATVIGCISADFQGGFEPYEEEDAERIFRRSTCTPTDQ

PCPYDESCCSGSCTYKANENGNQVKRCD
```

A polynucleotide encoding SEQ ID NO:52 is SEQ ID NO:53:

```
SEQ ID NO:53:
ATGAATACCG CTACAGGTTT CATCGTACTT TTGGTTTTGG

CGACAGTGAT CGGATGTATT TCTGCAGATT TTCAAGGAGG

TTTTGAACCT TATGAAGAAG AAGACGCCGA AAGAATATTT

CGCCGCTCAA CTTGCACTCC AACTGATCAA CCGTGCCCCT

ACGACGAAAG TTGCTGCAGC GGTTCCTGTA CATATAAGGC

AAATGAAAAC GGCAACCAAG TTAAAAGATG CGAC
```

The mature polypeptide toxin corresponding to SEQ ID NO:52 is SEQ ID NO:54:

```
SEQ ID NO:54:
STCTPTDQPCPYDESCCSGSCTYKANENGNQVKRCD
```

The invention includes isolated or purified omega-ACTX polypeptides. An "isolated" or "purified" polypeptide or fragment thereof is substantially free of cellular material or other contaminating polypeptides from the cell or tissue source from which the polypeptide is derived, or substantially free of chemical precursors or other chemicals when chemically synthesized. The language "substantially free of cellular material" includes preparations of polypeptide in which the polypeptide is separated from cellular components of the cells from which it is isolated or recombinantly produced. Thus, polypeptide that is substantially free of cellular material includes preparations of polypeptide having less than about 30%, about 20%, about 10%, or about 5% (by dry weight) of heterologous polypeptide (also referred to herein as a "contaminating polypeptide"). In one embodiment, the preparation is at least about 75% by weight pure, more specifically at least about 90% by weight pure, and most specifically at least about 95% by weight pure. A substantially pure omega-ACTX polypeptide may be obtained, for example, by extraction from a natural source (e.g., an insect cell); by expression of a recombinant nucleic acid encoding an omega-ACTX polypeptide; or by chemically synthesizing the polypeptide. Purity can be measured by an appropriate method, e.g., by column chromatography, polyacrylamide gel electrophoresis, or by high pressure liquid chromatography (HPLC) analysis.

The invention also includes homologs of omega-ACTX polypeptides. "Homolog" is a generic term used in the art to indicate a polynucleotide or polypeptide sequence possessing a high degree of sequence relatedness to a subject sequence. Such relatedness may be quantified by determining the degree of identity and/or similarity between the sequences being compared. Falling within this generic term are the terms "ortholog", meaning a polynucleotide or polypeptide that is the functional equivalent of a polynucleotide or polypeptide in another species, and "paralog" meaning a functionally similar sequence when considered within the same species. Paralogs present in the same species or orthologs of omega-ACTX genes in other species can readily be identified without undue experimentation, by molecular biological techniques well known in the art.

As used herein, "percent homology" of two amino acid sequences, or of two nucleic acids, is determined using the algorithm of Karlin and Altschul (1990) *Proc. Natl. Acad Sci., U.S.A.* 87: 2264-2268. Such an algorithm is incorporated into the NBLAST and XBLAST programs of Altschul et al. (1990) *J. Mol. Biol.* 215: 403-410. BLAST protein searches are performed with the XBLAST program, score=50, wordlength=3, to obtain amino acid sequences homologous to a reference polypeptide (e.g., SEQ ID NO:1). BLAST nucleotide searches are performed with the NBLAST program, score=100, wordlength 12, to obtain nucleotide sequences homologous to a nucleic acid molecule. To obtain gapped alignments for comparison purposes, Gapped BLAST is utilized as described in Altschul et al. (1997) *Nucleic Acids Res.* 25: 3389-3402. When utilizing BLAST and Gapped BLAST programs, the default parameters are typically used. (See http://www.ncbi.nlm.nih.gov)

Related polypeptides are aligned with omega-ACTX by assigning degrees of homology to various deletions, substitutions and other modifications. Homology can be determined along the entire polypeptide or polynucleotide, or along subsets of contiguous residues. The percent identity is the percentage of amino acids or nucleotides that are identical when the two sequences are compared. The percent similarity is the percentage of amino acids or nucleotides that are chemically similar when the two sequences are compared. Mature omega-ACTX and homologous polypeptides are preferably greater than or equal to about 70%, specifically greater than or equal to about 75%, specifically greater than or equal to about 80%, specifically greater than or equal to about 85%, more specifically greater than or equal to about 90%, and most specifically greater than or equal to about 95% identical. SEQ ID NO:1 or SEQ IS NO:2 may be employed as a reference polypeptide.

Where a particular polypeptide is said to have a specific percent identity to a reference polypeptide of a defined length, the percent identity is relative to the reference peptide. Thus, a polypeptide that is 50% identical to a reference polypeptide that is 100 amino acids long can be a 50 amino acid polypeptide that is completely identical to a 50 amino acid long portion of the reference polypeptide. It might also be a 100 amino acid long polypeptide that is 50% identical to the reference polypeptide over its entire length. Of course, many other polypeptides will meet the same criteria.

By "modification" of the primary amino acid sequence it is meant to include "deletions" (that is, polypeptides in which one or more amino acid residues are absent), "additions" (that is, a polypeptide which has one or more additional amino acid residues as compared to the specified polypeptide), "substitutions" (that is, a polypeptide which results from the replacement of one or more amino acid residues), and "fragments" (that is, a polypeptide consisting of a primary amino acid sequence which is identical to a portion of the primary sequence of the specified polypeptide). By "modification" it is also meant to include polypeptides that are altered as a result of post-translational events which change, for example, the glycosylation, amidation (e.g., C-terminal amidation), lipidation pattern, or the primary, secondary, or tertiary structure of the polypeptide. N-terminal and/or C-terminal modifications are possible.

Reference herein to either the nucleotide or amino acid sequence of omega-ACTX also includes reference to naturally occurring variants of these sequences. Nonnaturally occurring variants that differ from SEQ ID NOs: 7, 10, 13, 16, 19, 22, 25, 28, 31, 34, 37, 40, 43, 46, 49 or 52 for the prepropolypeptide, and SEQ ID NOs: 9, 12, 15, 18, 21, 24, 27, 30, 33, 36, 39, 42, 45, 48, 51 or 54 for the mature polypeptide, and retain biological function, are also included herein. The variants may comprise those polypeptides having conservative amino acid changes, i.e., changes of similarly charged or uncharged amino acids. Genetically encoded amino acids are generally divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cystine, serine, threonine, tyrosine). Phenylalanine, tryptophan, and tyrosine are sometimes classified jointly as aromatic amino acids. As each member of a family has similar physical and chemical properties as the other members of the same family, it is reasonable to expect that an isolated replacement of a leucine with an isoleucine or valine, an aspartate with a glutamate, a threonine with a serine, or a similar replacement of an amino acid with a structurally related amino acid will not have a major effect on the binding properties of the resulting molecule. Whether an amino acid change results in a functional polypeptide can readily be determined by assaying the acaricidal activity of the omega-ACTX polypeptide derivatives.

Reference to omega-ACTX also refers to polypeptide derivatives of omega-ACTX. As used herein, "polypeptide derivatives" include those polypeptides differing in length from a naturally-occurring omega-ACTX and comprising about fifteen or more amino acids in the same primary order as is found in omega-ACTX. Polypeptide derivatives can be longer than omega-ACTX, shorter than omega-ACTX (e.g., active fragments), so long as the polypeptide derivatives have acaricidal activity. Polypeptides having substantially the same amino acid sequence as omega-ACTX but possessing minor amino acid substitutions that do not substantially affect the acaricidal activity of omega-ACTX polypeptide derivatives, are within the definition of omega-ACTX polypeptide derivatives.

Homologs of omega-ACTX can be identified in several ways. In one method, native mRNA sequences encoding the precursors of omega-ACTX orthologs are identified by using standard molecular biology techniques to screen spider venom-gland cDNA libraries for such orthologs. The amino acid sequence of the mature omega-ACTX ortholog can be obtained from translation of the identified cDNA sequences by noting that endoproteolytic cleavage of the propeptide to give the mature toxin most likely occurs on the C-terminal side of an Arg-Arg processing site that immediately precedes the mature toxin (see second arrow in FIG. 1). Native mature omega-ACTX ortholog could then be isolated by chromatographic fractionation of the venom, followed by identification and purification of a peptide toxin with a mass matching that predicted from the omega-ACTX ortholog cDNA sequence. In another method, synthetic mature toxin could be produced by solid-phase peptide synthesis of the omega-ACTX sequence followed by cysteine oxidation to form the native disulfide isomer as described previously for production of synthetic J-atracotoxin-Hv1c (Wang et al. (2000) *Nature Structural Biolog* 7, 505-513). In one embodiment, an omega-ACTX polypeptide is oxidized and folded into its native three-dimensional structure by incubating the reduced, lyophilized peptide in a glutathione redox buffer. A suitable glutathione redox buffer includes 200 mM 3-[N-morpholino] propanesulphonic acid (MOPS) pH 7.3, 400 mM KCl, 2 mM EDTA, 4 mM reduced glutathione (GSH) and 2 mM oxidized glutathione (GSSG), although numerous variants are well known to those practiced in the art. This reaction mixture is, for example, incubated overnight at 4° C., room temperature, or 37° C., for example, and then fractionated using reverse-phase HPLC to separate individual disulfide isomers. Fractions are collected and assayed for acaricidal activity. In yet another method, the omega-ACTX ortholog is synthesized, chemically or by recombinant DNA techniques, from cDNA encoding the omega-ACTX ortholog. In another method, the omega-ACTX ortholog is prepared using recombinant DNA techniques by constructing a synthetic gene encoding the omega-ACTX sequence by methods known in the art.

The invention includes isolated omega-ACTX polynucleotides such as, for example, SEQ ID NOs: 8, 11, 14, 17, 20, 23, 26, 29, 32, 35, 38, 41, 44, 47, 50 or 53. The term "isolated polynucleotide" includes polynucleotides that are separated from other nucleic acid molecules present in the natural source of the nucleic acid. For example, with regard to genomic DNA, the term "isolated" includes polynucleotides that are separated from the chromosome with which the genomic DNA is naturally associated. An "isolated" polynucleotide is free of sequences which naturally flank the nucleic acid (i.e., sequences located at the 5' and/or 3' ends of the nucleic acid) in the genomic DNA of the organism from which the nucleic acid is derived. For example, in various embodiments, the isolated polynucleotide can contain less than about 5 kb, about 4 kb, about 3 kb, about 2 kb, about 1 kb, about 0.5 kb, or about 0.1 kb of 5' and/or 3' nucleotide sequences which naturally flank the nucleic acid molecule in genomic DNA of the cell from which the nucleic acid is derived. Moreover, an "isolated" polynucleotide, such as a cDNA molecule, can be substantially free of other cellular material, or culture medium when produced by recombinant techniques, or substantially free of chemical precursors or other chemicals when chemically synthesized. By free of other cellular material, it is meant that an isolated polynucleotide is greater than or equal to about 70%, about 75%, about 80%, about 85%, about 90%, about 95%, or about 99% pure.

"Polynucleotide" or "nucleic acid" refers to a polymeric form of nucleotides at least 5 bases in length. The nucleotides can be ribonucleotides, deoxyribonucleotides, or modified forms of either nucleotide. Modifications include but are not limited to known substitutions of a naturally-occurring base, sugar or internucleoside (backbone) linkage with a modified base such as 5-methylcytosine, a modified sugar such as 2'-methoxy and 2'-fluoro sugars, and modified backbones such as phosphorothioate and methyl phosphonate. As used herein, the term "gene" means the segment of DNA involved in producing a polypeptide chain; it includes regions preceding and following the coding region (leader and trailer) as well as intervening sequences (introns) between individual coding segments (exons).

The polynucleotide can be a DNA molecule, a cDNA molecule, a genomic DNA molecule, or an RNA molecule. The polynucleotide as DNA or RNA comprises a sequence wherein T can also be U. The polynucleotide can be complementary to a polynucleotide encoding an omega-ACTX polypeptide (e.g., SEQ ID NOs: 8, 11, 14, 17, 20, 23, 26, 29, 32, 35, 38, 41, 44, 47, 50 or 53), wherein complementary refers to the capacity for precise pairing between two nucleotides. For example, if a nucleotide at a certain position of a polynucleotide is capable of hydrogen bonding with a nucleotide at the same position in a DNA or RNA molecule, then the polynucleotide and the DNA or RNA molecule are complementary to each other at that position. The polynucleotide and the DNA or RNA molecule are substantially complementary to each other when a sufficient number of corresponding positions in each molecule are occupied by nucleotides that can hybridize with each other in order to effect the desired process. As used herein, hybridization means hydrogen bonding, which may be Watson-Crick, Hoogsteen or reversed Hoogsteen hydrogen bonding, between complementary nucleoside or nucleotide bases.

In addition, polynucleotides that are substantially identical to a polynucleotide encoding an omega-ACTX polypeptide (e.g., SEQ ID NOs: 8, 11, 14, 17, 20, 23, 26, 29, 32, 35, 38, 41, 44, 47, 50 or 53) or which encode proteins substantially identical to SEQ ID NOs: 1 and 2 are included. By "substantially identical" is meant a polypeptide or polynucleotide having a sequence that is at least about 85%, specifically about 90%, and more specifically about 95% or more identical to the sequence of the reference amino acid or nucleic acid sequence. For polypeptides, the length of the reference polypeptide sequence will generally be at least about 16 amino acids, or specifically at least about 20 amino acids, more specifically at least about 25 amino acids, and most specifically at least about 35 amino acids. For nucleic acids, the length of the reference nucleic acid sequence will generally be at least about 50 nucleotides, specifically at least about 60 nucleotides, more specifically at least about 75 nucleotides, and most specifically about 110 nucleotides.

Typically, homologous sequences to a polynucleotide can be confirmed by hybridization, wherein hybridization under stringent conditions as described, for example, in Sambrook et al., MOLECULAR CLONING: A LABORATORY MANUAL, 2d ed. (Cold Spring Harbor Press, Cold Spring Harbor, N.Y.) is preferred. Using the stringent hybridization outlined in Sambrook et al., (i.e., washing the nucleic acid fragments twice where each wash is at room temperature for 30 minutes with 2× sodium chloride and sodium citrate (SCC) and 0.1% sodium dodecyl sulfate (SDS); followed by washing one time at 50° C. for 30 minutes with 2×SCC and 0.1% SDS; and then washing two times where each wash is at room temperature for 10 minutes with 2×SCC), homologous sequences can be identified comprising at most about 25 to about 30% base pair mismatches, or about 15 to about 25% base pair mismatches, or about 5 to about 15% base pair mismatches.

A homologous polypeptide may be produced, for example, by conventional site-directed mutagenesis of polynucleotides (which is one avenue for routinely identifying residues of the molecule that are functionally important or not), by random mutation, by chemical synthesis, or by chemical or enzymatic cleavage of the polypeptides.

Polynucleotides encoding omega-ACTX sequences allow for the preparation of relatively short DNA (or RNA) sequences having the ability to specifically hybridize to such gene sequences. The short nucleic acid sequences may be used as probes for detecting the presence of complementary sequences in a given sample, or may be used as primers to detect, amplify or mutate a defined segment of the DNA sequences encoding an omega-ACTX polypeptide. A nucleic acid sequence employed for hybridization studies may be greater than or equal to about 14 nucleotides in length to ensure that the fragment is of sufficient length to form a stable and selective duplex molecule. Such fragments may be prepared by, for example, directly synthesizing the fragment by chemical means, by application of nucleic acid reproduction technology, such as PCR technology, or by excising selected nucleic acid fragments from recombinant plasmids containing appropriate inserts and suitable restriction sites.

The omega-ACTX and homolog polynucleotides can be inserted into a recombinant expression vector or vectors. The term "recombinant expression vector" refers to a plasmid, virus, or other means known in the art that has been manipulated by insertion or incorporation of the omega-AXTX genetic sequence. The term "plasmids" generally is designated herein by a lower case p preceded and/or followed by capital letters and/or numbers, in accordance with standard naming conventions that are familiar to those of skill in the art. Plasmids disclosed herein are either commercially available, publicly available on an unrestricted basis, or can be constructed from available plasmids by routine application of well-known, published procedures. Many plasmids and other cloning and expression vectors are well known and readily available, or those of ordinary skill in the art may readily construct any number of other plasmids suitable for use. These vectors may be transformed into a suitable host cell to form a host cell vector system for the production of a polypeptide.

The omega-ACTX polynucleotides can be inserted into a vector adapted for expression in a bacterial, plant, yeast, insect, amphibian, or mammalian cell that further comprises the regulatory elements necessary for expression of the nucleic acid molecule in the bacterial, yeast, insect, amphibian, plant, or mammalian cell operatively linked to the nucleic acid molecule encoding omega-ACTX. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., atg) in front of a protein-encoding gene, splicing signals for introns (if introns are present), maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter. By "promoter" is meant a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included.

If an expression vector is used to transform a plant, a promoter may be selected that has the ability to drive expression in the plant. Promoters that function in plants are well known in the art. Exemplary tissue-specific plant promoters are corn sucrose synthase-1 promoter, cauliflower mosaic virus (CaMV 35S) promoter, S-E9 small subunit RuBP carboxylase promoter, and corn heat shock protein promoter.

The choice of which expression vector, and ultimately to which promoter a polypeptide coding region is operatively linked, depends directly on the functional properties desired, for example, the location and timing of protein expression and the host cell to be transformed. In one embodiment, the vector used to express the polypeptide includes a selection marker that is effective in a plant cell. Transformation vectors used to transform plants and methods of making those vectors are described, for example, in U.S. Pat. Nos. 4,971,908, 4,940,835, 4,769,061 and 4,757,011, incorporated herein by reference.

The expression systems may also contain signal peptide and propolypeptide sequences that facilitate expression of the toxin gene and/or folding of the toxin. These could be the native omega-ACTX signal and propeptide sequences disclosed herein or other signal and/or propeptide sequences that serve the same purpose.

Insects which are susceptible to viral infection can be a target for insect viruses. The host range of an insect virus is at least in part determined by the natural host range of the unmodified, wild type virus. Insect viruses are naturally occurring insect pathogens. They may be DNA viruses or RNA viruses. Many insect viruses and their host range are known in the art, including viruses that are host-specific and environmentally safe. A suitable insect virus is a DNA virus which has been traditionally used as a biological control agent on insect pests, e.g., baculovirus (nucleopolyhedrovirus and granulovirus) and entomopoxvirus. For example, a baculovirus expression vector such as the type disclosed in U.S. Pat. No. 4,879,236, incorporated herein by reference, may be produced. Suitable RNA viruses include, but are not limited to cypovirus.

Vectors useful for expression of genes in higher plants are well known in the art and include vectors derived from the tumor-inducing (Ti) plasmid of *Agrobacterium tumefaciens* and pCaMVCN transfer control vector (available from Amersham Biosciences).

Transformation of a host cell with an expression vector or other DNA may be carried out by techniques well known to those skilled in the art. By "transformation" it is meant a permanent or transient genetic change induced in a cell following incorporation of new DNA (i.e., DNA exogenous to the cell). Where the cell is a mammalian cell, a permanent genetic change is generally achieved by introduction of the DNA into the genome of the cell. By "transformed cell" or "host cell" is meant a cell (e.g., prokaryotic or eukaryotic) into which (or into an ancestor of which) has been introduced, by means of recombinant DNA techniques, a DNA molecule encoding a polypeptide of the invention (i.e., an omega-ACTX polypeptide), or fragment thereof.

When the host is a eukaryote, methods of transfection with DNA such as calcium phosphate co-precipitates, mechanical procedures such as microinjection, electroporation, insertion of a plasmid encased in liposomes, or virus vectors, as well as others known in the art, may be used. When the host is a plant cell, other means of gene introduction into the cell may also be employed such as, for example, polyethylene glycol-mediated transformation of protoplasts, desiccation/inhibition-mediated DNA uptake, agitation with silicon carbide fibers, acceleration of DNA coated particles, injection into reproductive organs, and injection into immature embryos.

Eukaryotic cells can also be cotransfected with DNA sequences encoding a polypeptide of this disclosure, and a second foreign DNA molecule encoding a selectable phenotype, such as the herpes simplex thymidine kinase gene. Suitable markers include, for example, neomycin and hygromycin, and the like, that can be taken up by mammalian cells. Resistance to the marker can be conferred by the neomycin gene or the hygromycin gene, for example, when the gene has a suitable eukaryotic promoter. Another method is to use a eukaryotic viral vector, such as simian virus 40 (SV40), adenovirus, or bovine papilloma virus, to transiently infect or transform eukaryotic cells and express the protein. (*Eukaryotic Viral Vectors*, Cold Spring Harbor Laboratory, Gluzman ed., 1982). In one embodiment, a eukaryotic host is utilized as the host cell as described herein. The eukaryotic cell may be a yeast cell (e.g., *Saccharomyces cerevisiae*) or may be a mammalian cell, including a human cell.

Mammalian cell systems that utilize recombinant viruses or viral elements to direct expression may be engineered. For example, when using adenovirus expression vectors, the nucleic acid sequences encoding a foreign protein may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome will result in a recombinant virus that is viable and capable of expressing the omega-ACTX polypeptide in infected hosts.

For long-term, high-yield production of recombinant polypeptides, stable expression is preferred. Rather than using expression vectors that contain viral origins of replication, host cells can be transformed with the cDNA encoding an omega-ACTX fusion polypeptide controlled by appropriate expression control elements (e.g., promoter sequences, enhancer sequences, transcription terminators, polyadenylation sites, etc.), and a selectable marker. The selectable marker in the recombinant plasmid confers resistance to the selection and allows cells to stably integrate the plasmid into their chromosomes and grow to form foci, which in turn can be cloned and expanded into cell lines. For example, following the introduction of foreign DNA, engineered cells may be allowed to grow for 1 to 2 days in an enriched media, and then switched to a selective media. A number of selection systems may be used, including but not limited to the herpes simplex virus thymidine kinase, hypoxanthine-guanine phosphoribosyltransferase, and adenine phosphoribosyltransferase.

The omega-ACTX polypeptides can also be designed to provide additional sequences, such as, for example, the addition of coding sequences for added C-terminal or N-terminal amino acids that would facilitate purification by trapping on columns or use of antibodies. Such tags include, for example, histidine-rich tags that allow purification of polypeptides on nickel columns. Such gene modification techniques and suitable additional sequences are well known in the molecular biology arts.

Omega-ACTX proteins, polypeptides, or polypeptide derivatives can be purified by methods known in the art. These methods include, but are not limited to, size exclusion chromatography, ammonium sulfate fractionation, ion exchange chromatography, affinity chromatography, crystallization, electrofocusing, preparative gel electrophoresis, and combinations comprising one or more of the foregoing methods. Purification may be performed according to methods known to those of skill in the art that will result in a preparation of omega-ACTX substantially free from other polypeptides and from carbohydrates, lipids, or subcellular organelles. Purity may be assessed by means known in the art, such as SDS-polyacrylamide gel electrophoresis.

An omega-ACTX fusion polypeptide is also provided, comprising an omega-ACTX polypeptide covalently joined to a polypeptide to which it would not be joined in nature. Fusion polypeptides are useful for use in various assay systems. Therefore, fusion polypeptides may be used, for example, to detect omega-ACTX expression and to provide a defense mechanism for omega-ACTX expression when desired. For example, omega-ACTX fusion polypeptides can be used to identify proteins that interact with the omega-ACTX polypeptide and influence its function. This interaction may impart specificity to the ability of omega-ACTX to regulate other proteins, or it may increase or decrease the effect of omega-ACTX function. Physical methods, such as protein affinity chromatography, or library-based assays for protein-protein interactions, such as the yeast two-hybrid or phage display systems, can be used for this purpose. Such methods are well known in the art.

A fusion polypeptide comprises at least two heterologous polypeptide segments fused together by means of a peptide bond. The first polypeptide segment can comprise in whole or in part the contiguous amino acids of an omega-ACTX polypeptide. Where in part, at least about 8 contiguous amino acids of the omega-ACTX polypeptides are used, specifically at least about 10 may be employed, more specifically about 15, and most specifically at least about 20. The first polypeptide segment can also be a full-length omega-ACTX protein. The second polypeptide segment can comprise an enzyme which will generate a detectable product, such as beta-galactosidase or other enzymes that are known in the art. Alternatively, the second polypeptide segment can include a fluorescent protein such as green fluorescent protein, HcRed (Clontech) or other fluorescent proteins known in the art. Additionally, the fusion protein can be labeled with a detectable marker, such as a radioactive marker, a fluorescent marker, a chemiluminescent marker, a biotinylated marker, and the like.

Techniques for making fusion polypeptides, either recombinantly or by covalently linking two polypeptide segments are well known. Recombinant DNA methods can be used to construct omega-ACTX fusion polypeptides, for example, by making a DNA construct that comprises omega-ACTX coding sequence in proper reading frame with nucleotides encoding the second polypeptide segment and expressing the DNA construct in a host cell. The DNA construct can be operatively linked to sequences which facilitate protein production (i.e., promoters, etc.).

In addition to fusion polypeptides, omega-ACTX can be labeled in vitro by methods known in the art. Omega-ACTX can be conjugated to such dyes as Texas Red, rhodamine dyes, fluorescein and other dyes known in the art. Conjugation chemistries include succinimidyl ester, isothiocyanates, and maleimides. Detailed information about conjugatable dyes and conjugation chemistries can be found in the Molecular Probes Handbook of Fluorescent Probes and Research Products. Such fusion polypeptides can be used for the production of antibodies which may have greater specificity and sensitivity than those generated against short amino acid sequences. In addition, fusion polypeptides may be used to examine their ability to influence cell survival, proliferation and differentiation in tissue culture assays.

Transgenic plants may be constructed that express omega-ACTX polypeptide or the prepolypeptide or prepropolypeptide form of the toxin. By "transgenic plant" it is meant a plant, or progeny thereof, derived from a "transformed plant" cell or protoplast, wherein the plant DNA (nuclear or chloroplast) contains an introduced exogenous DNA molecule not originally present in a native, non-transgenic plant of the same strain.

The development or regeneration of plants from either single plant protoplasts or various explants is well known in the art. This regeneration and growth process typically includes the selection of transformed cells, and culturing those individualized cells through the usual stages of embryonic development through the rooted plantlet stage. Transgenic embryos and seeds may be similarly regenerated. The resulting transgenic rooted shoots may be thereafter planted in an appropriate plant growth medium such as soil.

The regenerated plants may be self-pollinated to provide homozygous transgenic plants. Otherwise, pollen obtained from the regenerated plants may be crossed to seed-grown plants of agronomically important, inbred lines. Conversely, pollen from plants of those important lines may be used to pollinate regenerated plants. A transgenic plant containing a desired polypeptide may be cultivated using methods well known to one skilled in the art.

A suitable transgenic plant includes an independent segregant that can transmit the omega-ACTX gene and its activity to its progeny. In one embodiment, a transgenic plant is homozygous for the omega-ACTX gene, and transmits that gene to all of its offspring on sexual mating. Seed from a transgenic plant may be grown in the field or greenhouse, and resulting sexually mature transgenic plants are self-pollinated to generate true breeding plants. The progeny from these plants become true breeding lines that are evaluated for, by way of example, increased acaricidal capacity against one or more acarines, preferably in the field, under a range of environmental conditions. The transgenic plant may be corn, soybeans, cotton, wheat, oats, barley, other grains, vegetables, fruits, fruit trees, berries, turf grass, ornamentals, shrubs and trees, and the like.

Libraries of mutated acaricidal polypeptides for the purposes of screening may be obtained by in vitro evolution of a gene for omega-ACTX-Hv1a, omega-ACTX-Hv2a or a variant. Libraries can be produced using error-prone PCR of the entire omega-ACTX or variant gene or digestion of the omega-ACTX or variant gene with an appropriate enzyme followed by error-prone PCR reconstruction of the entire gene sequence. These error-prone PCR procedures could also be applied to the complete prepropolypeptide gene sequence for omega-ACTX, or a variant.

The library of mutant omega-ACTX or variant gene sequences could then be used to generate a series of omega-ACTX variant antagonists. These antagonists may then be screened for their ability to inhibit the binding of omega-ACTX, or selected variant thereof, to its molecular target. Screening may be performed, for example, by phage display of a mutant gene library followed by selection of phage particles that bind tightly to the molecular target of omega-ACTX, or phage particles that inhibit the binding of omega-ACTX, or the selected variant thereof, to the molecular target of omega-ACTX. As would be understood by one of ordinary skill in the art, a mutant gene library could also be constructed by other standard molecular biological methods such as oligonucleotide cassette mutagenesis or construction of synthetic genes with certain nucleotide positions randomized.

The three-dimensional structure of omega-ACTX, and variants thereof, may also be used to search structure libraries for (or to design) either peptidic or non-peptidic compounds that resemble the key structural elements of omega-ACTX, particularly those regions found to be critical for activity by mutagenesis/truncation/modification experiments. These compounds could then be tested for their ability to inhibit the binding of omega-ACTX, or the variant thereof to its molecular target.

In one embodiment, there is provided an acaricidal composition comprising a purified omega-ACTX polypeptide and an agriculturally acceptable carrier. In another embodiment, an acaricidal composition comprises a virus expressing an omega-ACTX polypeptide. Infecting with a virus can be achieved via conventional methods, including ingestion, inhalation, direct contact with the insect virus, and the like.

The acaricidal composition may be in the form of a flowable solution or suspension such as an aqueous solution or suspension. Such aqueous solutions or suspensions may be provided as a concentrated stock solution which is diluted prior to application, or alternatively, as a diluted solution ready-to-apply. In another embodiment, an acaricidal composition comprises a water dispersible granule. In yet another embodiment, an acaricidal composition comprises a wettable powder, dust, pellet, or colloidal concentrate. Such dry forms of the acaricidal compositions may be formulated to dissolve immediately upon wetting, or alternatively, dissolve in a controlled-release, sustained-release, or other time-dependent manner.

The omega-ACTX polypeptides may be expressed in vitro and isolated for subsequent field application. Such polypeptides may be in the form of crude cell lysates, suspensions, colloids, etc., or may be purified, refined, buffered, and/or further processed, before formulating in an active acaricidal formulation.

Regardless of the method of application, the amount of the active component(s) are applied at an acaricidally-effective amount, which will vary depending on such factors as, for example, the specific acarines to be controlled, the specific host or environment to be treated, the environmental conditions, and the method, rate, and quantity of application of the acaricidally-active composition.

Acaricidal compositions comprising the omega-ACTX polypeptides, polynucleotides, etc., can be formulated with an agriculturally-acceptable carrier. Suitable agricultural carriers can be solid or liquid and are well known in the art. The term "agriculturally-acceptable carrier" covers all adjuvants, e.g., inert components, dispersants, surfactants, tackifiers, binders, etc., that are ordinarily used in insecticide formulation technology; these are well known to those skilled in pesticide formulation. The formulations may be mixed with one or more solid or liquid adjuvants and prepared by various means, e.g., by homogeneously mixing, blending and/or grinding the acaricidal composition with suitable adjuvants using conventional formulation techniques.

The acaricidal compositions may be employed singly or in combination with other compounds, including and not limited to other pesticides. They may be used in conjunction with other treatments such as surfactants, detergents, polymers or time-release formulations. The acaricidal compositions may comprise an acarine attractant. The acaricidal compositions may be formulated for either systemic or topical use. Such agents may also be applied to acarines directly.

The omega-ACTX polypeptides are particularly useful for methods involving controlling acarine pests. A method of controlling an acarine comprises contacting the locus of an acarine with an acaricidally effective amount of an omega-ACTX polypeptide. The omega-ACTX polypeptide may be in the form of a purified polypeptide, a polynucleotide encoding the omega-ACTX polypeptide optionally in an expression vector, a cell such as a plant cell or a bacterial cell expressing the omega-ACTX polypeptide, and/or a transgenic plant expressing the omega-ACTX polypeptide. Contacting includes, for example, injection of the omega-ACTX polypeptide, external contact, or ingestion of the omega-ACTX polypeptide or polynucleotide or virus expressing the omega-ACTX polypeptide.

The acaricidal compositions can be applied to the locus of the acarine pests. The "locus" of the mite, or tick refers to the acarine pest itself, or the environment in which the mite, or tick lives or where its eggs are present, including the air surrounding it, the food it eats, or objects or hosts which it contacts. The strength and duration of acaricidal application may be set with regard to conditions specific to the particular acarine pest(s) to be treated and particular environmental conditions. The proportional ratio of active ingredient to carrier will naturally depend on the chemical nature, solubilty, and stability of the acaricidal composition, as well as the particular formulation contemplated.

Subject to attack by ectoparasites such as ticks and mites are the numerous livestock animals, such as cattle, sheep, pigs, goats, buffalo, water buffalo, deer, rabbits, chickens, turkeys, ducks, geese, ostriches, and the like. Horses and other pleasure animals are subject to ectoparasitic attack, as are mink and other animals grown for their fur, and rats, mice and other animals used in laboratory and research settings. Companion animals such as dogs and cats are highly subject to attack by ectoparasites, and because of their close relationship with humans, such parasitism poses problems for the humans with whom they are associated.

Common practices for delivering an acaricide to livestock and companion animals include direct, whole-body treatment, where the animal's body is contacted with acaricide-containing liquids; systemic treatment, where the acaricide is allowed to circulate in the host's blood, including oral formulations, and implantable, controlled-release forms, for example; controlled-release systems, e.g., collars or ear tags, which are usually physically attached to the animal and which release pesticide continuously over a period of weeks or months; and self-medication methods, in which an animal is attracted to a device that offers a bait, e.g., food, materials for nest construction, etc., and which causes the animal to be sprayed or coated with acaricidal polypeptide. In the self-medication method, the animal either contacts the device or in some way triggers the device to release the pesticide.

Human beings are also potential hosts for many ectoparasites such as acarines, and in tropical areas and in areas with minimal sanitation, parasitic infections are a regular problem in medical practice. In the case of ticks, ticks may carry parasites and other infectious agents which can be transmitted to humans and/or animals. Tick-borne infections to which humans are susceptible include Lyme borreliosis, babesiosis and human granulocytic anaplasmosis. Scabies, in contrast, is an infestation of the skin with the microscopic mite *Sarcoptes scabei*. Acaricidal polypeptides can be administered to a human by ingestion or injection, for example.

In the case of tick-borne disease, transmittal to a human or animal host may occur via a wild animal vector such a deer or a mouse. Larvae live and feed on animals (e.g., rodents such as mice, deer, squirrels, livestock, and any humans who enter the tick habitat) for about a week before detaching and then molting (shedding) anywhere from 1 week to 8 months later. The larvae then become 8-legged nymphs. Nymphs feed on animals, engorge for 3 to 11 days, detach, and molt about a month later (depending on the species and environmental conditions). Once the nymph molts, it becomes an adult tick (male or female). Ticks climb up grass and plants and hold their legs up "sensing" and "looking" for their prey. Ticks insert their mouths, attach to their prey, and engorge themselves with a blood meal. During feeding, tick saliva can get into the host's body and blood stream. A tick infected with *Borrelia burgdorferi*, for example, can then inadvertently spread this bacteria to the host.

Because the life cycle of the tick is dependent upon animal vectors, one method of preventing tick-borne infections in humans and animals (farm animals and companion animals) is to administer the acaricidal polypeptides to the locus of an animal vector. The polypeptides can be administered to the animal vector, to the environment of the animal vector, or to the food of the animal vector, for example. In one embodiment, the acaricidal composition is administered in the form of a bait composition. A bait composition may include a feeding stimulant and, optionally, an attractant. An attractant is a material that is used to help bring a rodent or deer, for example, close to the bait. A feeding stimulant entices the rodent or deer, for example, to feed and to keep feeding on the bait. A material may function as both an attractant and a feeding stimulant. Attractants can be a food item or a "curiosity enhancer". The bait composition can be placed, for example, in brush or on residential properties to reduce tick populations.

In one embodiment, the acaricidal polypeptides are applied to the environment of an acarine. Application techniques suitable for treating the habitat of acarines include, for example, dusting, sprinkling, soaking, soil injection, seed coating, seedling coating, spraying, aerating, misting, atomizing, and the like. These application procedures are also well-known to those of skill in the art.

Parasitic mites infect the skin, for example, of humans and animals. Scabies, for example is infestation of the human skin with the microscopic mite *Sarcoptes scabei*. Mites such as those of the genus Psoroptes infect animals such as, for example, sheep and cause mange.

The acaricidal polypeptides can be used to control acarines that feed on plants such as phytophagous mites. Plant-feeding mites are among the most voracious phytophagous pests of crops. Plant-ingesting mites can be controlled by applying the active compound to plant parts which the mites eat or inhabit. The acaricidal polypeptides can be applied in a suitable manner known in the art, for example by spraying, atomizing, vaporizing, scattering, dusting, watering, squirting, sprinkling, pouring, fumigating, and the like. The dosage of the acaricidal polypeptide is dependent upon factors such as the type of pest, the carrier used, the method of application and climate conditions for application (e.g., indoors, arid, humid, windy, cold, hot, controlled), and the type of formulation (e.g., aerosol, liquid, or solid). The effective dosage, however, can be readily determined by persons of skill in the art.

In one embodiment, phytophagous mites can be controlled by the use of transgenic plants expressing the acaricidal polypeptides.

The acaricidal polypeptides can control acarines which typically inhabit an indoor area. Illustrative and non-limiting examples of acarines which can be controlled by using the acaricidal polypeptides include Dermanyssidae such as the American house dust mite (*Dermatophagoides farinae*) and *Dermatophagoides pternonyssinus*, Acaridae such as *Lardoglyphus konoi*, mold or copra or forage mite (*Tyrophagus putrescentiae*) and brown legged grain mite (*Aleuroglyphus ovatus*), Glycyphagidae such as *Glycyphagus privatus, Glycyphagus domesticus*, groceries mite (*Glycyphagus destuctor*), and *Chortoglyphus* spp., Cheyletidae such as *Chelacaropsis moorei, Chelacaropsis malaccensis, Cheyletus fortis, Cheyletus eruditus* and *Chelatomorpha lepidoterorum*, Macronyssidae such as *Ornithonyssus bacoti, Ornithonyssus sylviarum, Dermanyssus gallinae* and *Dermanyssus hirundinis*, Haplochthonius simplex, Pyemotidae, and Sarcoptidae, and the like.

In the treatment of indoor acarine pests, the acaricidal polypeptides can be applied to an indoor environment, for example, sprayed onto textile surfaces such as sofas, upholstered chairs, bedding, pillows, rugs, carpets, etc. known to be infested with dust mites. Although emphasis is placed on dust mites and their allergens, it should be understood that these methods are equally effective against dust particles in general and against other allergens associated therewith, including pollen and animal dander. Application may be by means of a self-contained aerosol spraying device. Spraying should be carefully done, ensuring that, for example, all sides of pillows are sprayed, that the spray reaches to corners and crevices, etc.

The invention is further illustrated by the following non-limiting examples.

EXAMPLE 1

Discovery of Omega-ACTX-1 Family Polypeptides

A female *Hadronyche infensa* spider was collected from the city of Toowoomba in the state of Queensland, Australia. A female *Hadronyche versuta* spider was obtained from the Blue Mountains region of New South Wales, Australia. Male and female *Atrax robustus* spiders were collected from the Sydney metropolitan area of New South Wales, Australia. The specimens were housed in airtight collection jars until extraction of venom glands. The funnel web spiders were cooled to −20° C. for 40 to 60 minutes. Venom glands were independently dissected from each specimen. Each pair of venom glands was independently placed in extraction buffer (Amersham Biosciences).

Immediately following venom gland isolation, poly A+ mRNA was prepared using a QuickPrep™ Micro mRNA Purification Kit (Amersham Biosciences). The purified mRNA samples were washed with 80% ethanol and dried with a Speedvac. 10 microliters of RNAse-free distilled water obtained from a cDNA synthesis kit (Amersham Biosciences) was used to rehydrate the mRNA samples. The purified mRNA samples were stored at −20° C.

Thereafter, cDNA libraries were constructed using a Marathon™ cDNA Amplification Kit (CLONTECH). From the adapted mRNA template, single-stranded cDNA was constructed using Superscript™ III reverse transcriptase (Life Technologies, Inc) and Echoclonanch-2 primer, a poly (dT) anchor primer (GGGCAGGT$_{17}$) (SEQ ID NO: 58). Second strand synthesis was carried out according to the kit specifications. cDNA products were purified using Concert™ Rapid PCR Purification kit (GIBCO). The double stranded cDNA was eluted with 50 µl of Tris-EDTA buffer (10 mM Tris-Cl, 1 mM EDTA, pH 8.0).

The Marathon™ cDNA Amplification adaptor (CLONTECH) was then ligated to the double stranded cDNA. The ligation reaction was allowed to take place at 16° C. overnight. After overnight ligation, the sample was precipitated using 10 µl of a 1 to 20 dilution of glycogen, 10 µl of 3 M sodium acetate pH 5.2, and 100 µl of 100% cold ethanol. Subsequently, the sample was washed with 80% ethanol and dried for 10 minutes prior to resuspension in 200 µl of Tris-EDTA buffer.

Leader sequence information was obtained using 5' RACE (Rapid Amplification of cDNA Ends; see Frohman et al., Rapid production of full-length cDNAs from rare transcripts: amplification using a single gene-specific oligonucleotide primer, Proceedings of the National Academy of Sciences USA 85, 8993-9002, 1988). 5' RACE is used to extend partial cDNA clones by amplifying the 5' sequences of the corresponding mRNA. 5' RACE uses knowledge of only a small region of sequence within the partial cDNA clone. 5' RACE employs a first round of cDNA extension by the enzyme terminal transferase, which adds a homopolymeric tail to the 5' end of all template cDNAs. This synthetic tail provides a primer-binding site upstream of the unknown 5' sequence of the target mRNA. A PCR reaction is then carried out, which uses a general sense primer that binds to the new 5' tail and a specific antisense primer that binds to the known cDNA sequence. Redundant polymerase chain reaction (PCR) primers were designed for this technique. The redundant primers were used in conjunction with a 5' universal adaptor primer (EchoAP1) in order to obtain unknown leader sequence information. Primers for 3' RACE were designed from the cDNA leader sequence obtained from 5' RACE. 3' RACE primers were used in combination with a universal adaptor oligo d(T) primer (CLONTECH) to generate gene products that have a signal sequence homologous with that of omega-ACTX-Hv1a. All primers not included in kits were constructed by PROLIGO Ltd.

The 5' RACE primers were as follows:

```
SEQ ID NO:55:
CACCCCTAATACGACTCACTATAGG

SEQ ID NO:56:
RTTNCCRTTYTCRTTYTCYTCRAA
```

wherein R=puRines (A/G degeneracy), Y=pYrimidines (C/T degeneracy), and N=complete degeneracy (A, G, C, or T).

The 3' RACE primers were as follows:

```
SEQ ID NO:57:
TGCTGCAATATGAATACCGC

SEQ ID NO:58:
GGGCAGGTTTTTTTTTTTTTTTTT
```

PCR reactions were conducted using 5 μl double stranded cDNA, 27 μl Milli Q water, 25 mM $MgCl_2$, 10× PCR buffer, 50× dNTPs, and 5 μl $AMPLI_{GOLD}$TAQ™ Enzyme (Perkin Elmer, AmpliTaq™ Gold with GeneAmp Kit). PCR reactions were run on a thermal cycler using the following protocol:

| Cycle Temperature | Time | Number of Cycles |
|---|---|---|
| 95° C. | 5 minutes | 1 |
| 95° C. | 30 seconds | 35 |
| 55° C. | 60 seconds | 35 |
| 72° C. | 90 seconds | 35 |
| 72° C. | 10 minutes | 1 |
| 30° C. | 1 minutes | 1 |

Amplified cDNA products were electrophoresed on a 1.5% agarose gel and stained with ethidium bromide for size verification.

Verified PCR products were extracted from the agarose gel using a GIBCO gel purification kit and precipitated using Pellet Paint® Co-Precipitant kit (Novagen). Once precipitated, cDNA ends were phosphorylated with kinase in preparation for cloning. Samples were ligated into the pSMART™ vector and transformed into *E. cloni* cells (Lucigen) using the Lucigen CloneSmart Blunt Cloning kit. Successfully transformed clones were cultured for one hour in Terrific Broth with 50 μg/mL ampicillin, and then plated to allow for overnight growth.

The samples were tested for the correct insert size by PCR and gel electrophoresis. Samples containing the correct insert size were submitted for DNA sequencing. Complete cDNA sequences encoding the preproprotein form of omega-ACTX-Hv1a (SEQ ID No:1) and 16 paralogs thereof (SEQ ID NO: 7, 10, 13, 16, 19, 22, 25, 28, 31, 34, 37, 40, 43, 46, 49 or 52) were obtained from sequencing numerous clones. These preproprotein sequences are summarized and aligned in FIG. 1. The signal peptide cleavage site in these preproproteins was predicted using version 3.0 of the SignalP program (Dryløv et al., Improved prediction of signal peptides: SignalP 3.0, *Journal of Molecular Biology* 340, 783-795, 2004; program available on the web at http://www.cbs.dtu.dk/services/SignalP/). The mature toxin is predicted to result from cleavage of the propeptide following the dibasic Arg-Arg sequence at positions 36-37, as for the known propeptide cleavage site in the ω-ACTX-1 toxins produced by Australian funnel-web spiders. These two endoproteolytic cleavage sites are indicated by arrows in FIG. 1.

EXAMPLE 2

Preparation of Recombinant Omega-ACTX-Hv1a

Recombinant omega-ACTX-Hv1a was prepared as described in Tedford et al., Functional significance of the beta-hairpin in the insecticidal neurotoxin omega-atracotoxin-Hv1a. *J. Biol. Chem.* 276, 26568-26576, 2001. Briefly, *Escherichia coli* BL21 cells were transformed with pHWT1 for overproduction of the GST:omega-ACTX-Hv1a fusion protein. Cells were grown in LB medium at 37° C. to an $OD_{600}$ of 0.6-0.8 before induction of the fusion protein with 150 μM isopropyl-β-D-thiogalactopyranoside (IPTG). Cells were harvested by centrifugation 3-4 hours after induction and lysed using a French press. The recombinant fusion protein was purified from the soluble cell fraction using affinity chromatography on GSH-Sepharose (Amersham Biosciences) and then cleaved on the column by the addition of bovine thrombin (Sigma) for about 24 hours. The unbound toxin was eluted from the column with Tris-buffered saline (150 mM NaCl, 50 mM Tris, pH 8.0) and immediately purified using reverse phase high-performance liquid chromatography (rpHPLC). Recombinant toxin and contaminants were eluted from a Vydac $C_{18}$ analytical rpHPLC column (4.6×250 mm, 5 μm pore size) at a flow rate of 1 ml $min^{-1}$ using a linear gradient of 12.5-20% acetonitrile over 20 minutes. A single major peak corresponding to omega-ACTX-Hv1a eluted at a retention time of approximately 11 minutes. Note that the recombinant toxin contains two additional N-terminal residues (Gly-Ser) relative to the native protein, which are a vestige of the thrombin cleavage site in the GST fusion protein.

EXAMPLE 3

Purification of Native Omega-ACTX-Hv2a

Native omega-ACTX-Hv2a is purified from the venom of the Australian funnel-web spider *Hadronyche versuta* exactly as described in Wang et al., Discovery and structure of a potent and highly specific blocker of insect calcium channels, *J. Biol. Chem.* 276, 40806-40812, 2001. Briefly, lyophilized crude venom is fractionated using a Vydac C18 analytical reverse phase high pressure liquid chromatography (rpHPLC) column. Semi-pure omega-ACTX-Hv2a obtained from this initial fractionation is further purified on the same column using a gradient of 30-48% acetonitrile over about 35 min at a flow rate of about 1 ml/min. Once purified to greater than about 98% homogeneity, peptides are lyophilized and stored at 20° C. until further use.

EXAMPLE 4

Recombinant Omega-ACTX-Hv1a is Lethal to Ticks by Injection

The acaricidal activity of recombinant omega-ACTX-Hv1a was determined quantitatively by direct injection of toxin into the lone star tick *Amblyomma americanum* (Arachnida: Ixodida:Ixodidae). Ticks were obtained from a laboratory-bred, pathogen-free colony of *Amblyomma americanum* maintained at 27±1° C. and 75% relative humidity in the Department of Immunology, University of Connecticut Health Center. *A. americanum* is an important vector of zoonotic human pathogens in the United States. It is responsible for transmitting the causative agents of human ehrlichioses (*Ehrlichia chaffeensis* and *E. ewingii*) and southern tick-associated rash illness (*Borrelia lonestari*), a clinical condition similar to Lyme disease. It may also serve as a vector for the causative agents of tularemia (*Francisella tularensis*) and Rocky Mountain spotted fever (*Rickettsia rickettsii*).

Dose-response curves were constructed by injecting doses in the range 200-1200 picomoles of toxin per gram of tick. The toxin has a molecular weight of about 4200 Daltons, so this corresponds to about 0.8-5 micrograms of toxin per gram of tick. The toxin was dissolved in insect saline (200 mM NaCl, 3.1 mM KCl, 5.4 mM $CaCl_2$, 5.0 mM $MgCl_2$, 2 mM $NaHCO_3$, and 0.1 mM $NaH_2PO_4$, pH 7.2) to give a stock solution of sufficient concentration that each dose required injection of no more than 2 microliters of stock solution. Specimens were temporarily immobilized at 4° C. for the injections. Following injection, each tick was housed individually in a vial in a 27° C. humidified chamber. A cohort of 6-8 ticks were injected for each toxin dose, and a cohort of 6-8 control ticks were injected with just the vehicle (insect saline). Injections were performed using a Hamilton microsyringe (Hamilton Co., Reno, Nev.). Death was scored at 48 hours. The severity and onset of symptoms varied with the dose and route of administration, although at high doses severe effects were observed within a few minutes. The most pronounced phenotypic effect was curling of all eight legs into closed loops; this made locomotion extremely difficult although ticks could walk very slowly on the bent limbs at low toxin does. Ticks also lost their righting reflex, possibly due to general limb weakness and the "curling" phenotype described above. At higher toxin doses (>1000 pmol/g), the integument of treated ticks became black, and moribund ticks were paralyzed in the resting position. This immobilizing (paralyzing) effect of the toxin was irreversible.

Figure 2:
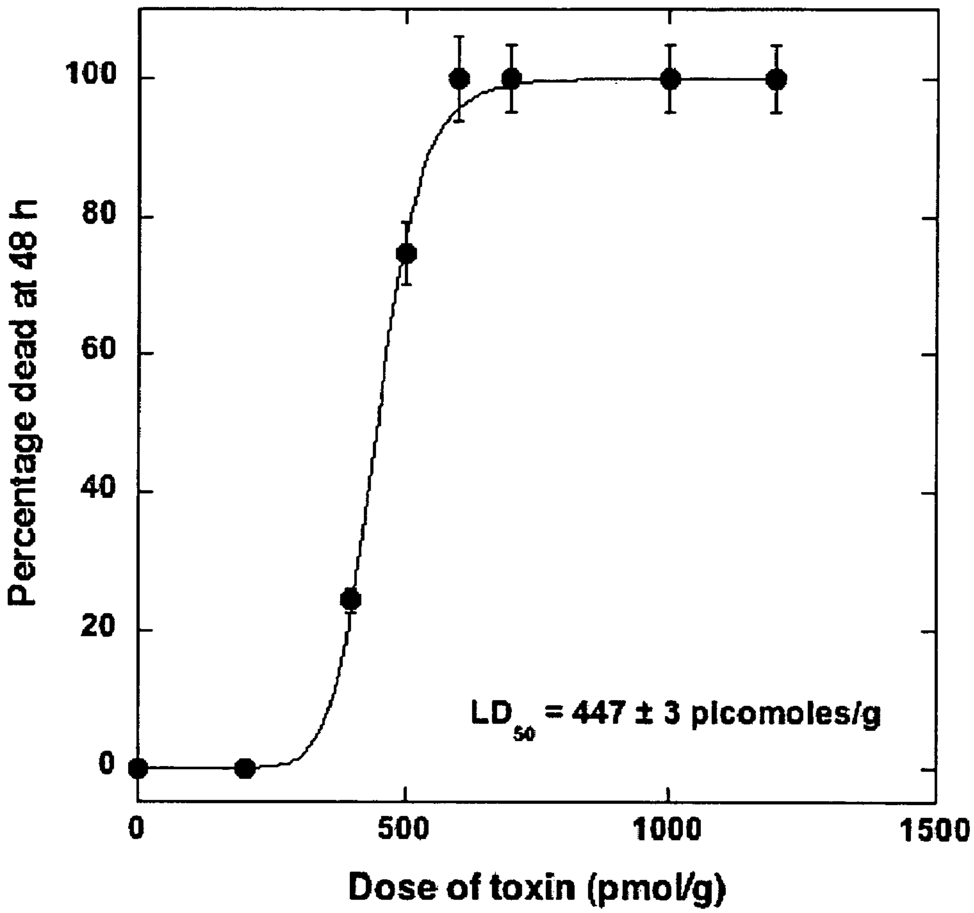
FIG. 2 is a dose-response curve resulting from injection of recombinant omega-ACTX-Hv1a into the lone star tick *Amblyomma americanum*.

FIG. 2 shows the dose-response curve obtained for omega-ACTX-Hv1a using this method. Each point represents the average of three independent measurements performed on different days. The $LD_{50}$ value (i.e., the dose of omega-ACTX-Hv1a that kills 50% of ticks at 48 hours post-injection) was calculated by fitting the following equation to the log dose-response curve:

$$y=(a-b)/[1+(x/LD_{50})^n]$$

where y is the percentage deaths in the sample population at 48 hours post-injection, x is the toxin dose in $pmolg^{-1}$, n is a variable slope factor, a is the maximum response and b is the minimum response. The calculated $LD_{50}$ value was 447±3 $pmolg^{-1}$.

EXAMPLE 5

Recombinant Omega-ACTX-Hv1a is Lethal to Ticks by Feeding

The oral acaricidal activity of recombinant omega-ACTX-Hv1a was determined quantitatively by feeding the toxin to the lone star tick *Amblyomma americanum* using doses in the range 400-1400 picomoles of toxin per gram of tick. The toxin has a molecular weight of about 4200 Daltons, so this corresponds to about 1.7-6 micrograms of toxin per gram of tick. For the feeding experiments, the toxin was dissolved in Roswell Park Memorial Institute (RPMI)-1640 medium and ticks were fed 2-3 microliters of this solution from a 5 microliter capillary tube (WR Scientific, West Chester, Pa.). RPMI medium comprises:

| Components | g/L |
|---|---|
| L-Arginine [Free Base] | 0.2 |
| L-Asparagine [Anhydrous] | 0.05 |

-continued

| Components | g/L |
|---|---|
| L-Aspartic Acid | 0.02 |
| L-Cystine•2HCl | 0.0652 |
| L-Glutamic Acid | 0.02 |
| L-Glutamine | 0.3 |
| Glycine | 0.01 |
| L-Histidine [Free Base] | 0.015 |
| Hydroxy-L-Proline | 0.02 |
| L-Isoleucine | 0.05 |
| L-Leucine | 0.05 |
| L-Lysine•HCl | 0.04 |
| L-Methionine | 0.015 |
| L-Phenylalanine | 0.015 |
| L-Proline | 0.02 |
| L-Serine | 0.03 |
| L-Threonine | 0.02 |
| L-Tryptophan | 0.005 |
| L-Tyrosine•Na•2$H_2O$ | 0.02883 |
| L-Valine | 0.02 |
| Biotin | 0.0002 |
| Choline Chloride | 0.003 |
| Folic Acid | 0.001 |
| Myo-Inositol | 0.035 |
| Niacinamide | 0.001 |
| D-Pantothenic Acid Hemicalcium | 0.00025 |
| PABA | 0.001 |
| Pyridoxi•HCl | 0.001 |
| Riboflavin | 0.0002 |
| Thiamine•HCl | 0.001 |
| Vitamin B12 | 0.000005 |
| Calcium Nitrate•$H_2O$ | 0.1 |
| Magnesium Sulfate [Anhydrous] | 0.04884 |
| Potassium Chloride | 0.4 |
| Sodium Chloride | 6.0 |
| Sodium Phosphate Dibasic [Anhydrous] | 0.8 |
| D-Glucose | 2.0 |
| Glutathione, Reduced | 0.001 |
| Phenol Red•Na | 0.0053 |

Capillary tubes were polished to give a bevelled surface that was inserted over the chelicerae and hypostome, which comprise the tick's mouthparts. Care was taken to ensure that ticks did not become dehydrated during feeding experiments. A cohort of 6-8 ticks were fed for each toxin dose, and a cohort of 6-8 control ticks were fed with just the vehicle (RPMI-1640). Death was scored at 48 hours, but symptoms were seen with higher doses within a few minutes, and the ticks became quickly paralyzed. The most unusual symptom of intoxication was bending of the limbs into a closed loop. Ticks also lost their righting reflex. Control ticks were unaffected by the ingestion of RPMI-1640.

Figure 3:
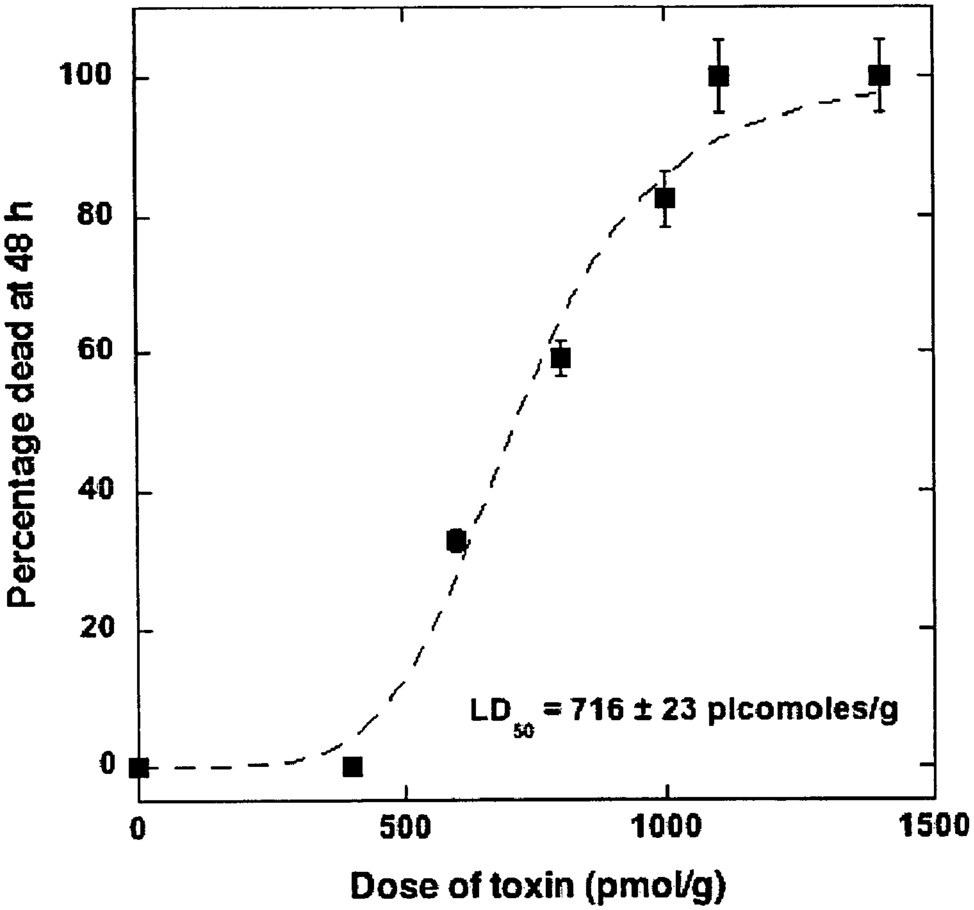
FIG. 3 is a dose-response curve resulting from feeding recombinant omega-ACTX-Hv1a to the lone star tick *Amblyomma americanum.*

FIG. 3 shows the dose-response curve obtained from feeding omega-ACTX-Hv1a to *A. americanum*. Each point represents the average of three independent measurements performed on different days. The $LD_{50}$ value (i.e., the dose of omega-ACTX-Hv1a that kills 50% of ticks at 48 hours post-injection) was calculated by fitting the following equation to the log dose-response curve:

$$y=(a-b)/[1+(x/LD_{50})^n]$$

where y is the percentage deaths in the sample population at 48 hours post-injection, x is the toxin dose in $pmolg^{-1}$, n is a variable slope factor, a is the maximum response and b is the minimum response. The calculated $LD_{50}$ value for oral delivery of the toxin was 716±23 $pmolg^{-1}$, which is less than two-fold higher than the $LD_{50}$ obtained with direct injection of the toxin (FIG. 3).

Ticks fed toxin-laced RPMI medium exhibited peculiar behavior that was not evidenced by control ticks fed toxin-free RPMI medium. Ticks fed toxin-laced RPMI medium tried to dislodge the capillary tube containing the medium, and they consumed a smaller quantity of liquid (average of 2-3 μl) over the 60 min feeding period as compared to control ticks (average of 4-6 μl). Furthermore, the test cohort took significantly longer to drink this smaller volume of RPMI medium (50-60 min) compared with control ticks (25-30 min). Thus, the $LD_{50}$ calculated for oral administration of omega-ACTX-Hv1a is almost certainly an overestimate, which implies that the toxin is virtually equipotent when delivered via this route as compared to when it is injected into ticks. Moreover, these results indicate that omega-ACTX-Hv1a, in addition to being highly toxic to ticks, may also be an effective anti-feedant.

EXAMPLE 6

Native Omega-ACTX-Hv2a is Lethal to Ticks by Injection

The acaricidal activity of native omega-ACTX-Hv2a was determined by direct injection of a single dose of toxin (6 nmol/g, about 25 μg/g) into a cohort of five unengorged male or five unengorged female *A. americanum*. The toxin was dissolved in insect saline to give a stock solution of sufficient concentration that the injection volume was less than 2 microliters. A cohort of five ticks were injected with just the vehicle (insect saline). Specimens were temporarily immobilized at 4° C. for the injections, then each tick was housed individually in a vial in a 27° C. humidified chamber. In ticks injected with toxin, symptoms were seen within a few minutes, and the ticks quickly became irreversibly paralyzed. The most unusual symptom of intoxication was bending of the limbs into a closed loop. Ticks also lost their righting reflex. There was 100% mortality in both the male and female tick populations at 48 hours. In contrast, control ticks were unaffected by the injection of insect saline.

As has been shown herein, acarine pests such as ticks can be effectively controlled using acaricidal polypeptides. The polypeptides may comprise the omega-ACTX-1 and omega-ACTX-2 families previously shown to have insecticidal activity. Given that insects and ticks are not closely related, the acaricidal activity of the polypeptides was unexpected.

The terms "first," "second," and the like, herein do not denote any order, quantity, or importance, but rather are used to distinguish one element from another, and the terms "a" and "an" herein do not denote a limitation of quantity, but rather denote the presence of at least one of the referenced item. All ranges disclosed herein are inclusive and combinable.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

All cited patents, patent applications, and other references are incorporated herein by reference in their entirety.

The invention claimed is:

1. A method of controlling acarine pests, comprising applying an effective amount of an isolated polypeptide, or a composition comprising an isolated polypeptide to a locus of the acarine pests, wherein the polypeptide is an omega-ACTX peptide having greater than or equal to 70% sequence identity to SEQ ID NO: 1; capable of forming three intrachain disulfide bonds; and having six conserved cysteine residues at positions corresponding to amino acid positions 4, 11, 17, 18, 22 and 36 of SEQ ID NO:1.

2. The method of claim 1, wherein the polypeptide is any one of SEQ ID NOS: 9, 12, 15, 18, 21, 27, 30, 33, 36, 39, 42, 45, 48, 51 or 54.

3. The method of claim 1, wherein the isolated polypeptide or the composition comprising the isolated polypeptide, is applied to a locus of the acarine pests, wherein the locus is an animal vector of the pests.

4. The method of claim 3, wherein the animal vector comprises a deer or a rodent.

5. The method of claim 1, wherein the isolated polypeptide, or the composition comprising the isolated polypeptide, is in the form of a bait composition.

6. The method of claim 1, wherein the acarine pest comprises a phytophagous mite and wherein the composition is applied to a plant part which the mites eat or inhabit.

7. The method of claim 1, wherein the acarine pest is a tick capable of bearing a pathogen that infects humans, farm animals, or companion animals.

8. The method of claim 1, wherein the acarine pest is a mite that is parasitic to humans or animals.

9. The method of claim 1, wherein the acarine pest is a dust mite and wherein the composition is applied to an indoor environment.

10. A method of inhibiting acarine pest infestation in a farm animal, a companion animal, or an animal vector comprising applying a composition comprising an effective amount of an isolated polypeptide to a locus of the acarine pests, wherein the polypeptide is an omega-ACTX peptide having greater than or equal to 70% sequence identity to SEQ ID NO: 1; capable of forming three intrachain disulfide bonds; and having six conserved cysteine residues at positions corresponding to amino acid positions 4, 11, 17, 18, 22 and 36 of SEQ ID NO:1.

* * * * *

```
                         SEQUENCE LISTING


<160> NUMBER OF SEQ ID NOS: 58

<210> SEQ ID NO 1
<211> LENGTH: 37
<212> TYPE: PRT
<213> ORGANISM: Hadronyche versuta

<400> SEQUENCE: 1

Ser Pro Thr Cys Ile Pro Ser Gly Gln Pro Cys Pro Tyr Asn Glu Asn
1               5                   10                  15

Cys Cys Ser Gln Ser Cys Thr Phe Lys Glu Asn Glu Asn Gly Asn Thr
            20                  25                  30

Val Lys Arg Cys Asp
        35


<210> SEQ ID NO 2
<211> LENGTH: 45
<212> TYPE: PRT
<213> ORGANISM: Hadronyche versuta

<400> SEQUENCE: 2

Leu Leu Ala Cys Leu Phe Gly Asn Gly Arg Cys Ser Ser Asn Arg Asp
1               5                   10                  15

Cys Cys Glu Leu Thr Pro Val Cys Lys Arg Gly Ser Cys Val Ser Ser
            20                  25                  30

Gly Pro Gly Leu Val Gly Gly Ile Leu Gly Gly Ile Leu
        35                  40                  45


<210> SEQ ID NO 3
<211> LENGTH: 22
```

-continued

<212> TYPE: PRT
<213> ORGANISM: Hadronyche versuta
<220> FEATURE:
<221> NAME/KEY: Xaa
<222> LOCATION: (7)..(7)
<223> OTHER INFORMATION: V or F
<220> FEATURE:
<221> NAME/KEY: Xaa
<222> LOCATION: (21)..(21)
<223> OTHER INFORMATION: S or E

<400> SEQUENCE: 3

Met Asn Thr Ala Thr Gly Xaa Ile Ala Leu Leu Val Leu Ala Thr Val
1 5 10 15

Ile Gly Cys Ile Xaa Ala
20

<210> SEQ ID NO 4
<211> LENGTH: 19
<212> TYPE: PRT
<213> ORGANISM: Hadronyche versuta

<400> SEQUENCE: 4

Glu Asp Thr Arg Ala Asp Leu Gln Gly Gly Glu Ala Ala Glu Lys Val
1 5 10 15

Phe Arg Arg

<210> SEQ ID NO 5
<211> LENGTH: 20
<212> TYPE: PRT
<213> ORGANISM: Hadronyche versuta
<220> FEATURE:
<221> NAME/KEY: Xaa
<222> LOCATION: (3)..(3)
<223> OTHER INFORMATION: Q or E
<220> FEATURE:
<221> NAME/KEY: Xaa
<222> LOCATION: (5)..(5)
<223> OTHER INFORMATION: G or S
<220> FEATURE:
<221> NAME/KEY: Xaa
<222> LOCATION: (8)..(8)
<223> OTHER INFORMATION: P or S
<220> FEATURE:
<221> NAME/KEY: Xaa
<222> LOCATION: (9)..(9)
<223> OTHER INFORMATION: Y or S
<220> FEATURE:
<221> NAME/KEY: Xaa
<222> LOCATION: (10)..(10)
<223> OTHER INFORMATION: E or absent
<220> FEATURE:
<221> NAME/KEY: Xaa
<222> LOCATION: (11)..(11)
<223> OTHER INFORMATION: G, E or V

<400> SEQUENCE: 5

Asp Phe Xaa Gly Xaa Phe Glu Xaa Xaa Xaa Xaa Glu Asp Ala Glu Arg
1 5 10 15

Ile Phe Arg Arg
20

<210> SEQ ID NO 6
<211> LENGTH: 15
<212> TYPE: PRT
<213> ORGANISM: Hadronyche versuta

<400> SEQUENCE: 6

Gly Glu Ser His Val Arg Glu Asp Ala Met Gly Arg Ala Arg Arg

-continued

```
1               5                   10                  15


<210> SEQ ID NO 7
<211> LENGTH: 78
<212> TYPE: PRT
<213> ORGANISM: Atrax robustus

<400> SEQUENCE: 7

Met Asn Thr Ala Thr Gly Val Ile Ala Leu Leu Val Leu Ala Thr Val
1               5                   10                  15

Ile Gly Cys Ile Glu Ala Glu Asp Thr Arg Ala Asp Leu Gln Gly Gly
            20                  25                  30

Glu Ala Ala Glu Lys Val Phe Arg Arg Ser Pro Thr Cys Ile Pro Ser
        35                  40                  45

Gly Gln Pro Cys Pro Tyr Asn Glu Asn Cys Cys Ser Gln Ser Cys Thr
    50                  55                  60

Phe Lys Glu Asn Glu Asn Gly Asn Thr Val Lys Arg Cys Asp
65                  70                  75


<210> SEQ ID NO 8
<211> LENGTH: 234
<212> TYPE: DNA
<213> ORGANISM: Atrax robustus

<400> SEQUENCE: 8

atgaataccg ctacaggtgt catcgctctt ttggttctgg cgacagtcat cggatgcatt      60

gaagcagaag ataccagagc agatcttcaa ggaggagaag ccgccgagaa agtatttcgc     120

cgctccccga cttgcattcc atctggtcaa ccatgtccct acaacgaaaa ttgctgcagc     180

caatcgtgta catttaagga aaatgaaaac ggcaacactg ttaaaagatg cgac           234


<210> SEQ ID NO 9
<211> LENGTH: 37
<212> TYPE: PRT
<213> ORGANISM: Atrax robustus

<400> SEQUENCE: 9

Ser Pro Thr Cys Ile Pro Ser Gly Gln Pro Cys Pro Tyr Asn Glu Asn
1               5                   10                  15

Cys Cys Ser Gln Ser Cys Thr Phe Lys Glu Asn Glu Asn Gly Asn Thr
            20                  25                  30

Val Lys Arg Cys Asp
        35


<210> SEQ ID NO 10
<211> LENGTH: 78
<212> TYPE: PRT
<213> ORGANISM: Atrax robustus

<400> SEQUENCE: 10

Met Asn Thr Ala Thr Gly Val Ile Ala Leu Leu Val Leu Val Thr Val
1               5                   10                  15

Ile Gly Cys Ile Glu Ala Glu Asp Thr Arg Ala Asp Leu Gln Gly Gly
            20                  25                  30

Glu Ala Ala Glu Lys Val Phe Arg Arg Ser Pro Thr Cys Ile Pro Ser
        35                  40                  45

Gly Gln Pro Cys Pro Tyr Asn Glu Asn Cys Cys Ser Gln Ser Cys Thr
    50                  55                  60

Phe Lys Glu Asn Glu Asn Gly Asn Thr Val Lys Arg Cys Asp
```

-continued 65 70 75

<210> SEQ ID NO 11
<211> LENGTH: 234
<212> TYPE: DNA
<213> ORGANISM: Atrax robustus

<400> SEQUENCE: 11
atgaataccg ctacaggtgt catcgctctt ttggttctgg tgacagtcat cggatgcatt 60
gaagcagaag ataccagagc agatcttcaa ggaggagaag ccgccgagaa agtatttcgc 120
cgctccccga cttgcattcc atctggtcaa ccatgtccct acaacgaaaa ttgctgcagc 180
caatcgtgta catttaagga aaatgaaaac ggcaacactg ttaaaagatg cgac 234

<210> SEQ ID NO 12
<211> LENGTH: 37
<212> TYPE: PRT
<213> ORGANISM: Atrax robustus

<400> SEQUENCE: 12

Ser Pro Thr Cys Ile Pro Ser Gly Gln Pro Cys Pro Tyr Asn Glu Asn
1 5 10 15

Cys Cys Ser Gln Ser Cys Thr Phe Lys Glu Asn Glu Asn Gly Asn Thr
20 25 30

Val Lys Arg Cys Asp
35

<210> SEQ ID NO 13
<211> LENGTH: 78
<212> TYPE: PRT
<213> ORGANISM: Atrax robustus

<400> SEQUENCE: 13

Met Asn Thr Ala Thr Gly Val Ile Ala Leu Leu Val Leu Ala Thr Val
1 5 10 15

Ile Gly Cys Ile Glu Ala Glu Asp Thr Arg Ala Asp Leu Gln Gly Gly
20 25 30

Glu Ala Ala Glu Lys Val Phe Arg Arg Ser Pro Thr Cys Ile Pro Ser
35 40 45

Gly Gln Pro Cys Pro Tyr Asn Glu Asn Cys Cys Ser Gln Ser Cys Thr
50 55 60

Phe Lys Glu Asn Glu Thr Gly Asn Thr Val Lys Arg Cys Asp
65 70 75

<210> SEQ ID NO 14
<211> LENGTH: 234
<212> TYPE: DNA
<213> ORGANISM: Atrax robustus

<400> SEQUENCE: 14
atgaataccg ctacaggtgt catcgctctt ttggttctgg cgacagtcat cggatgcatt 60
gaagcagaag ataccagagc agatcttcaa ggaggagaag ccgccgagaa agtatttcgc 120
cgctccccga cttgcattcc atctggtcaa ccatgtccct acaacgaaaa ttgctgcagc 180
caatcgtgta catttaagga aaatgaaacc ggcaacactg ttaaaagatg cgac 234

<210> SEQ ID NO 15
<211> LENGTH: 37
<212> TYPE: PRT
<213> ORGANISM: Atrax robustus

<400> SEQUENCE: 15

```
Ser Pro Thr Cys Ile Pro Ser Gly Gln Pro Cys Pro Tyr Asn Glu Asn
1               5                   10                  15

Cys Cys Ser Gln Ser Cys Thr Phe Lys Glu Asn Glu Thr Gly Asn Thr
            20                  25                  30

Val Lys Arg Cys Asp
        35
```

<210> SEQ ID NO 16
<211> LENGTH: 78
<212> TYPE: PRT
<213> ORGANISM: Atrax robustus

<400> SEQUENCE: 16

```
Met Asn Thr Ala Thr Gly Val Ile Ala Leu Leu Val Leu Ala Thr Val
1               5                   10                  15

Ile Gly Cys Ile Glu Ala Glu Asp Thr Arg Ala Asp Leu Gln Gly Gly
            20                  25                  30

Glu Ala Ala Glu Lys Val Phe Arg Arg Ser Pro Thr Cys Ile Pro Ser
        35                  40                  45

Gly Gln Pro Cys Pro Tyr Asn Glu Asn Cys Cys Ser Gln Ser Cys Thr
    50                  55                  60

Phe Lys Glu Asn Glu Asn Ala Asn Thr Val Lys Arg Cys Asp
65                  70                  75
```

<210> SEQ ID NO 17
<211> LENGTH: 234
<212> TYPE: DNA
<213> ORGANISM: Atrax robustus

<400> SEQUENCE: 17

```
atgaataccg ctacaggtgt catcgctctt ttggttctgg cgacagtcat cggatgcatt     60

gaagcagaag ataccagagc agatcttcaa ggaggagaag ccgccgagaa agtatttcgc    120

cgctccccga cttgcattcc atctggtcaa ccatgtccct acaacgaaaa ttgctgcagc    180

caatcgtgta catttaagga aaatgaaaac gccaacactg ttaaaagatg cgac          234
```

<210> SEQ ID NO 18
<211> LENGTH: 37
<212> TYPE: PRT
<213> ORGANISM: Atrax robustus

<400> SEQUENCE: 18

```
Ser Pro Thr Cys Ile Pro Ser Gly Gln Pro Cys Pro Tyr Asn Glu Asn
1               5                   10                  15

Cys Cys Ser Gln Ser Cys Thr Phe Lys Glu Asn Glu Asn Ala Asn Thr
            20                  25                  30

Val Lys Arg Cys Asp
        35
```

<210> SEQ ID NO 19
<211> LENGTH: 78
<212> TYPE: PRT
<213> ORGANISM: Atrax robustus

<400> SEQUENCE: 19

```
Met Asn Thr Ala Thr Gly Val Ile Ala Leu Leu Val Leu Ala Thr Val
1               5                   10                  15
```

-continued

```
Ile Gly Cys Ile Glu Ala Glu Asp Thr Arg Ala Asp Leu Gln Gly Gly
            20                  25                  30

Glu Ala Ala Glu Lys Val Phe Arg Arg Ser Pro Thr Cys Ile Pro Ser
        35                  40                  45

Gly Gln Pro Cys Pro Tyr Asn Glu Asn Cys Cys Ser Lys Ser Cys Thr
    50                  55                  60

Tyr Lys Glu Asn Glu Asn Gly Asn Thr Val Gln Arg Cys Asp
65                  70                  75


<210> SEQ ID NO 20
<211> LENGTH: 234
<212> TYPE: DNA
<213> ORGANISM: Atrax robustus

<400> SEQUENCE: 20

atgaataccg ctacaggtgt catcgctctt ttggttctgg cgacagtcat cggatgcatt      60

gaagcagaag ataccagagc agatcttcaa ggaggagaag ccgccgagaa agtatttcgc     120

cgctccccga cttgcattcc atctggtcaa ccatgtccct acaacgaaaa ttgctgcagc     180

aaatcgtgta catataagga aaatgaaaat ggcaacactg ttcaaagatg cgac           234


<210> SEQ ID NO 21
<211> LENGTH: 37
<212> TYPE: PRT
<213> ORGANISM: Atrax robustus

<400> SEQUENCE: 21

Ser Pro Thr Cys Ile Pro Ser Gly Gln Pro Cys Pro Tyr Asn Glu Asn
1               5                   10                  15

Cys Cys Ser Lys Ser Cys Thr Tyr Lys Glu Asn Glu Asn Gly Asn Thr
            20                  25                  30

Val Gln Arg Cys Asp
        35


<210> SEQ ID NO 22
<211> LENGTH: 73
<212> TYPE: PRT
<213> ORGANISM: Atrax robustus

<400> SEQUENCE: 22

Met Asn Thr Ala Thr Gly Phe Ile Val Leu Leu Val Leu Ala Thr Val
1               5                   10                  15

Leu Gly Cys Ile Glu Ala Gly Glu Ser His Val Arg Glu Asp Ala Met
            20                  25                  30

Gly Arg Ala Arg Arg Gly Ala Cys Thr Pro Thr Gly Gln Pro Cys Pro
        35                  40                  45

Tyr Asn Glu Ser Cys Cys Ser Gly Ser Cys Gln Glu Gln Leu Asn Glu
    50                  55                  60

Asn Gly His Thr Val Lys Arg Cys Val
65                  70


<210> SEQ ID NO 23
<211> LENGTH: 219
<212> TYPE: DNA
<213> ORGANISM: Atrax robustus

<400> SEQUENCE: 23

atgaataccg caacaggttt cattgtcctt ttggttttgg cgacagttct tggatgcatt      60

gaagcaggag aatctcatgt gagagaagac gccatgggaa gagctcgccg gggggcttgc     120
```

actccaactg gtcaaccgtg cccgtataac gaaagttgtt gcagcggttc ctgccaagaa 180
cagctaaatg aaaacggaca cactgttaaa agatgcgtt 219

<210> SEQ ID NO 24
<211> LENGTH: 36
<212> TYPE: PRT
<213> ORGANISM: Atrax robustus

<400> SEQUENCE: 24

Gly Ala Cys Thr Pro Thr Gly Gln Pro Cys Pro Tyr Asn Glu Ser Cys
1 5 10 15

Cys Ser Gly Ser Cys Gln Glu Gln Leu Asn Glu Asn Gly His Thr Val
20 25 30

Lys Arg Cys Val
35

<210> SEQ ID NO 25
<211> LENGTH: 79
<212> TYPE: PRT
<213> ORGANISM: Hadronyche versuta

<400> SEQUENCE: 25

Met Asn Thr Ala Thr Gly Phe Ile Val Leu Leu Val Leu Ala Thr Val
1 5 10 15

Ile Gly Cys Ile Ser Ala Asp Phe Gln Gly Gly Phe Glu Pro Tyr Glu
20 25 30

Gly Glu Asp Ala Glu Arg Ile Phe Arg Arg Ser Pro Thr Cys Ile Pro
35 40 45

Thr Gly Gln Pro Cys Pro Tyr Asn Glu Asn Cys Cys Ser Gln Ser Cys
50 55 60

Thr Tyr Lys Ala Asn Glu Asn Gly Asn Gln Val Lys Gly Cys Asp
65 70 75

<210> SEQ ID NO 26
<211> LENGTH: 237
<212> TYPE: DNA
<213> ORGANISM: Hadronyche versuta

<400> SEQUENCE: 26
atgaataccg ctacaggttt catcgtactt ttggttttgg cgacagtgat cggatgcatt 60
tctgcagatt ttcaaggagg tttcgaacct tatgaaggag aagacgccga aagaatattt 120
cgccgctccc caacttgcat tccaactggt caaccgtgtc cctacaacga aaattgctgc 180
agccaatcct gtacatataa ggcaaatgaa aacggcaacc aagttaaagg atgcgac 237

<210> SEQ ID NO 27
<211> LENGTH: 37
<212> TYPE: PRT
<213> ORGANISM: Hadronyche versuta

<400> SEQUENCE: 27

Ser Pro Thr Cys Ile Pro Thr Gly Gln Pro Cys Pro Tyr Asn Glu Asn
1 5 10 15

Cys Cys Ser Gln Ser Cys Thr Tyr Lys Ala Asn Glu Asn Gly Asn Gln
20 25 30

Val Lys Gly Cys Asp
35

-continued

<210> SEQ ID NO 28
<211> LENGTH: 79
<212> TYPE: PRT
<213> ORGANISM: Hadronyche versuta

<400> SEQUENCE: 28

Met Asn Thr Ala Thr Gly Phe Ile Val Leu Leu Val Leu Ala Thr Val
1 5 10 15

Ile Gly Cys Ile Ser Ala Asp Phe Gln Gly Gly Phe Glu Pro Tyr Glu
20 25 30

Glu Glu Asp Ala Glu Arg Ile Phe Arg Arg Ser Pro Thr Cys Ile Pro
35 40 45

Thr Gly Gln Pro Cys Pro Tyr Asn Glu Asn Cys Cys Asn Gln Ser Cys
50 55 60

Thr Tyr Lys Ala Asn Glu Asn Gly Asn Gln Val Lys Arg Cys Asp
65 70 75

<210> SEQ ID NO 29
<211> LENGTH: 237
<212> TYPE: DNA
<213> ORGANISM: Hadronyche versuta

<400> SEQUENCE: 29
atgaataccg ctacaggttt catcgtactt ttggttttgg cgacagtgat cggatgcatt 60
tctgcagatt ttcaaggagg tttcgaacct tatgaagaag aagacgccga aagaatattt 120
cgccgctccc caacttgcat tccaactggt caaccgtgtc cctacaacga aaattgctgc 180
aaccaatcct gtacatataa ggcaaatgaa aacggcaacc aagttaaaag atgcgac 237

<210> SEQ ID NO 30
<211> LENGTH: 37
<212> TYPE: PRT
<213> ORGANISM: Hadronyche versuta

<400> SEQUENCE: 30

Ser Pro Thr Cys Ile Pro Thr Gly Gln Pro Cys Pro Tyr Asn Glu Asn
1 5 10 15

Cys Cys Asn Gln Ser Cys Thr Tyr Lys Ala Asn Glu Asn Gly Asn Gln
20 25 30

Val Lys Arg Cys Asp
35

<210> SEQ ID NO 31
<211> LENGTH: 79
<212> TYPE: PRT
<213> ORGANISM: Hadronyche versuta

<400> SEQUENCE: 31

Met Asn Thr Ala Thr Gly Phe Ile Val Leu Leu Val Leu Ala Thr Val
1 5 10 15

Ile Gly Cys Ile Ser Ala Asp Phe Gln Gly Gly Phe Glu Pro Tyr Glu
20 25 30

Glu Glu Asp Ala Glu Arg Ile Phe Arg Arg Ser Pro Thr Cys Ile Pro
35 40 45

Thr Gly Gln Pro Cys Pro Tyr Asn Glu Asn Cys Cys Ser Gln Ser Cys
50 55 60

Thr Tyr Lys Ala Asn Glu Asn Gly Asn Gln Val Lys Arg Cys Asp
65 70 75

-continued

<210> SEQ ID NO 32
<211> LENGTH: 237
<212> TYPE: DNA
<213> ORGANISM: Hadronyche versuta

<400> SEQUENCE: 32
atgaataccg ctacaggttt catcgtactt ttggttttgg cgacagtgat cggatgcatt 60
tctgcagatt ttcaaggagg tttcgaacct tatgaagaag aagacgccga aagaatattt 120
cgccgctccc caacttgcat tccaactggt caaccgtgtc cctacaacga aaattgctgc 180
agccaatcct gtacatataa ggcaaatgaa aacggcaacc aagttaaaag atgcgac 237

<210> SEQ ID NO 33
<211> LENGTH: 37
<212> TYPE: PRT
<213> ORGANISM: Hadronyche versuta

<400> SEQUENCE: 33

Ser Pro Thr Cys Ile Pro Thr Gly Gln Pro Cys Pro Tyr Asn Glu Asn
1 5 10 15

Cys Cys Ser Gln Ser Cys Thr Tyr Lys Ala Asn Glu Asn Gly Asn Gln
20 25 30

Val Lys Arg Cys Asp
35

<210> SEQ ID NO 34
<211> LENGTH: 79
<212> TYPE: PRT
<213> ORGANISM: Hadronyche versuta

<400> SEQUENCE: 34

Met Asn Thr Ala Thr Gly Phe Ile Val Leu Leu Val Leu Ala Thr Val
1 5 10 15

Ile Gly Cys Ile Ser Val Asp Phe Gln Gly Gly Phe Glu Ser Tyr Glu
20 25 30

Glu Glu Asp Ala Glu Arg Ile Phe Arg Arg Ser Pro Thr Cys Ile Pro
35 40 45

Thr Gly Gln Pro Cys Pro Tyr Asn Glu Asn Cys Cys Ser Gln Ser Cys
50 55 60

Thr Tyr Lys Ala Asn Glu Asn Gly Asn Gln Val Lys Arg Cys Asp
65 70 75

<210> SEQ ID NO 35
<211> LENGTH: 237
<212> TYPE: DNA
<213> ORGANISM: Hadronyche versuta

<400> SEQUENCE: 35
atgaataccg ctacaggttt catcgtactt ttggttttgg cgacagtgat cggatgtatt 60
tctgtagatt ttcaaggagg tttcgaatct tatgaagaag aagacgccga aagaatattt 120
cgccgctccc caacttgcat tccaactggt caaccgtgtc cctacaacga aaattgctgc 180
agccaatcct gtacatataa ggcaaatgaa aacggcaacc aagttaaaag atgcgac 237

<210> SEQ ID NO 36
<211> LENGTH: 37
<212> TYPE: PRT
<213> ORGANISM: Hadronyche versuta

<400> SEQUENCE: 36

-continued

```
Ser Pro Thr Cys Ile Pro Thr Gly Gln Pro Cys Pro Tyr Asn Glu Asn
1               5                   10                  15

Cys Cys Ser Gln Ser Cys Thr Tyr Lys Ala Asn Glu Asn Gly Asn Gln
            20                  25                  30

Val Lys Arg Cys Asp
        35


<210> SEQ ID NO 37
<211> LENGTH: 78
<212> TYPE: PRT
<213> ORGANISM: Hadronyche versuta

<400> SEQUENCE: 37

Met Asn Thr Ala Thr Gly Phe Ile Val Leu Leu Val Leu Ala Thr Val
1               5                   10                  15

Ile Gly Cys Ile Ser Ala Asp Phe Gln Gly Gly Phe Glu Ser Ser Val
            20                  25                  30

Glu Asp Ala Glu Arg Leu Phe Arg Arg Ser Ser Thr Cys Ile Arg Thr
        35                  40                  45

Asp Gln Pro Cys Pro Tyr Asn Glu Ser Cys Cys Ser Gly Ser Cys Thr
    50                  55                  60

Tyr Lys Ala Asn Glu Asn Gly Asn Gln Val Lys Arg Cys Asp
65                  70                  75


<210> SEQ ID NO 38
<211> LENGTH: 234
<212> TYPE: DNA
<213> ORGANISM: Hadronyche versuta

<400> SEQUENCE: 38

atgaataccg ctacaggttt catcgttctt ttggttttgg cgacagtgat cggatgcatt      60

tctgcagatt ttcaaggagg tttcgaatct tctgtagaag acgccgaaag attatttcgc     120

cgctcctcaa cttgcattcg aactgatcaa ccgtgcccct acaacgaaag ttgctgcagc     180

ggttcctgta catataaggc aaatgaaaac ggaaaccaag ttaaaagatg cgac           234


<210> SEQ ID NO 39
<211> LENGTH: 37
<212> TYPE: PRT
<213> ORGANISM: Hadronyche versuta

<400> SEQUENCE: 39

Ser Ser Thr Cys Ile Arg Thr Asp Gln Pro Cys Pro Tyr Asn Glu Ser
1               5                   10                  15

Cys Cys Ser Gly Ser Cys Thr Tyr Lys Ala Asn Glu Asn Gly Asn Gln
            20                  25                  30

Val Lys Arg Cys Asp
        35


<210> SEQ ID NO 40
<211> LENGTH: 78
<212> TYPE: PRT
<213> ORGANISM: Hadronyche versuta

<400> SEQUENCE: 40

Met Asn Thr Ala Thr Gly Phe Ile Val Leu Leu Val Leu Ala Thr Val
1               5                   10                  15

Ile Gly Cys Ile Ser Ala Asp Phe Gln Gly Gly Phe Glu Pro Tyr Glu
            20                  25                  30
```

-continued

```
Glu Glu Asp Ala Glu Arg Ile Phe Arg Arg Ser Thr Cys Thr Pro Thr
        35                  40                  45

Asp Gln Pro Cys Pro Tyr His Glu Ser Cys Cys Ser Gly Ser Cys Thr
    50                  55                  60

Tyr Lys Ala Asn Glu Asn Gly Asn Gln Val Lys Arg Cys Asp
65                  70                  75


<210> SEQ ID NO 41
<211> LENGTH: 234
<212> TYPE: DNA
<213> ORGANISM: Hadronyche versuta

<400> SEQUENCE: 41

atgaataccg ctacaggttt catcgtactt ttggttttgg cgacagtgat cggatgcatt      60

tctgcagatt ttcaaggagg tttcgaacct tatgaagaag aagacgccga aagaatattt     120

cgccgctcaa cttgcactcc aactgatcaa ccgtgcccct accacgaaag ttgctgcagc     180

ggttcctgta catataaggc aaatgaaaac ggcaaccaag ttaaaagatg cgac           234


<210> SEQ ID NO 42
<211> LENGTH: 36
<212> TYPE: PRT
<213> ORGANISM: Hadronyche versuta

<400> SEQUENCE: 42

Ser Thr Cys Thr Pro Thr Asp Gln Pro Cys Pro Tyr His Glu Ser Cys
1               5                   10                  15

Cys Ser Gly Ser Cys Thr Tyr Lys Ala Asn Glu Asn Gly Asn Gln Val
            20                  25                  30

Lys Arg Cys Asp
        35


<210> SEQ ID NO 43
<211> LENGTH: 78
<212> TYPE: PRT
<213> ORGANISM: Hadronyche versuta

<400> SEQUENCE: 43

Met Asn Thr Ala Thr Gly Phe Ile Val Leu Leu Val Leu Ala Thr Val
1               5                   10                  15

Ile Gly Cys Ile Ser Ala Asp Phe Glu Gly Ser Phe Glu Pro Tyr Glu
            20                  25                  30

Glu Glu Asp Ala Glu Arg Ile Phe Arg Arg Ser Thr Cys Thr Pro Thr
        35                  40                  45

Asp Gln Pro Cys Pro Tyr Asp Glu Ser Cys Cys Ser Gly Ser Cys Thr
    50                  55                  60

Tyr Lys Ala Asn Glu Asn Gly Asn Gln Val Lys Arg Cys Asp
65                  70                  75


<210> SEQ ID NO 44
<211> LENGTH: 234
<212> TYPE: DNA
<213> ORGANISM: Hadronyche versuta

<400> SEQUENCE: 44

atgaataccg ctacaggttt catcgtactt ttggttttgg cgacagtgat cggatgcatt      60

tctgctgatt ttgaaggaag tttcgaacct tatgaagaag aagacgccga aagaatattt     120

cgccgctcaa cttgcactcc aactgatcaa ccgtgcccct acgacgaaag ttgctgcagc     180
```

-continued

```
ggttcctgta catataaggc aaatgaaaac ggcaaccaag ttaaaagatg cgac          234


<210> SEQ ID NO 45
<211> LENGTH: 36
<212> TYPE: PRT
<213> ORGANISM: Hadronyche versuta

<400> SEQUENCE: 45

Ser Thr Cys Thr Pro Thr Asp Gln Pro Cys Pro Tyr Asp Glu Ser Cys
1               5                   10                  15

Cys Ser Gly Ser Cys Thr Tyr Lys Ala Asn Glu Asn Gly Asn Gln Val
            20                  25                  30

Lys Arg Cys Asp
        35


<210> SEQ ID NO 46
<211> LENGTH: 78
<212> TYPE: PRT
<213> ORGANISM: Hadronyche versuta

<400> SEQUENCE: 46

Met Asn Thr Ala Thr Gly Phe Ile Val Leu Leu Val Leu Ala Thr Val
1               5                   10                  15

Ile Gly Cys Ile Ser Ala Asp Phe Gln Gly Ser Phe Glu Pro Tyr Glu
            20                  25                  30

Glu Glu Asp Ala Glu Arg Ile Phe Arg Arg Ser Thr Cys Thr Pro Thr
        35                  40                  45

Asp Gln Pro Cys Pro Tyr Asp Glu Ser Cys Cys Ser Gly Ser Cys Thr
    50                  55                  60

Tyr Lys Ala Asn Glu Asn Gly Asn Gln Val Lys Arg Cys Asp
65                  70                  75


<210> SEQ ID NO 47
<211> LENGTH: 234
<212> TYPE: DNA
<213> ORGANISM: Hadronyche versuta

<400> SEQUENCE: 47

atgaataccg ctacaggttt catcgttctt ttggttttgg cgacagtgat cggatgcatt     60

tctgcagatt ttcaaggaag tttcgaacct tatgaagaag aagacgccga aagaatattt    120

cgccgctcaa cttgcactcc aactgatcaa ccgtgcccct acgacgaaag ttgctgcagc    180

ggttcctgta catataaggc aaatgaaaac ggcaaccaag ttaaaagatg tgac          234


<210> SEQ ID NO 48
<211> LENGTH: 36
<212> TYPE: PRT
<213> ORGANISM: Hadronyche versuta

<400> SEQUENCE: 48

Ser Thr Cys Thr Pro Thr Asp Gln Pro Cys Pro Tyr Asp Glu Ser Cys
1               5                   10                  15

Cys Ser Gly Ser Cys Thr Tyr Lys Ala Asn Glu Asn Gly Asn Gln Val
            20                  25                  30

Lys Arg Cys Asp
        35


<210> SEQ ID NO 49
<211> LENGTH: 78
<212> TYPE: PRT
```

-continued

<213> ORGANISM: Hadronyche versuta

<400> SEQUENCE: 49

Met Asn Thr Ala Thr Gly Phe Ile Val Leu Leu Val Leu Ala Thr Val
1 5 10 15

Ile Gly Cys Ile Ser Ala Asp Phe Gln Gly Ser Phe Glu Pro Tyr Glu
20 25 30

Glu Glu Asp Ala Glu Arg Ile Phe Arg Arg Ser Thr Cys Thr Pro Thr
35 40 45

Asp Gln Pro Cys Pro Tyr His Glu Ser Cys Cys Ser Gly Ser Cys Thr
50 55 60

Tyr Lys Ala Asn Glu Asn Gly Asn Gln Val Lys Arg Cys Asp
65 70 75

<210> SEQ ID NO 50
<211> LENGTH: 234
<212> TYPE: DNA
<213> ORGANISM: Hadronyche versuta

<400> SEQUENCE: 50
atgaataccg ctacaggttt catcgtactt ttggttttgg cgacagtgat cggatgcatt 60
tctgcagatt ttcaaggaag tttcgaacct tatgaagaag aagacgccga aagaatattt 120
cgccgctcaa cttgcactcc aactgatcaa ccgtgcccct accacgaaag ttgctgcagc 180
ggttcctgta catataaggc aaatgaaaac ggcaaccaag ttaaaagatg cgac 234

<210> SEQ ID NO 51
<211> LENGTH: 36
<212> TYPE: PRT
<213> ORGANISM: Hadronyche versuta

<400> SEQUENCE: 51

Ser Thr Cys Thr Pro Thr Asp Gln Pro Cys Pro Tyr His Glu Ser Cys
1 5 10 15

Cys Ser Gly Ser Cys Thr Tyr Lys Ala Asn Glu Asn Gly Asn Gln Val
20 25 30

Lys Arg Cys Asp
35

<210> SEQ ID NO 52
<211> LENGTH: 78
<212> TYPE: PRT
<213> ORGANISM: Hadronyche versuta

<400> SEQUENCE: 52

Met Asn Thr Ala Thr Gly Phe Ile Val Leu Leu Val Leu Ala Thr Val
1 5 10 15

Ile Gly Cys Ile Ser Ala Asp Phe Gln Gly Gly Phe Glu Pro Tyr Glu
20 25 30

Glu Glu Asp Ala Glu Arg Ile Phe Arg Arg Ser Thr Cys Thr Pro Thr
35 40 45

Asp Gln Pro Cys Pro Tyr Asp Glu Ser Cys Cys Ser Gly Ser Cys Thr
50 55 60

Tyr Lys Ala Asn Glu Asn Gly Asn Gln Val Lys Arg Cys Asp
65 70 75

<210> SEQ ID NO 53
<211> LENGTH: 234
<212> TYPE: DNA

-continued

<213> ORGANISM: Hadronyche versuta

<400> SEQUENCE: 53
atgaataccg ctacaggttt catcgtactt ttggttttgg cgacagtgat cggatgtatt 60
tctgcagatt ttcaaggagg ttttgaacct tatgaagaag aagacgccga aagaatattt 120
cgccgctcaa cttgcactcc aactgatcaa ccgtgcccct acgacgaaag ttgctgcagc 180
ggttcctgta catataaggc aaatgaaaac ggcaaccaag ttaaaagatg cgac 234

<210> SEQ ID NO 54
<211> LENGTH: 36
<212> TYPE: PRT
<213> ORGANISM: Hadronyche versuta

<400> SEQUENCE: 54

Ser Thr Cys Thr Pro Thr Asp Gln Pro Cys Pro Tyr Asp Glu Ser Cys
1 5 10 15

Cys Ser Gly Ser Cys Thr Tyr Lys Ala Asn Glu Asn Gly Asn Gln Val
20 25 30

Lys Arg Cys Asp
35

<210> SEQ ID NO 55
<211> LENGTH: 25
<212> TYPE: DNA
<213> ORGANISM: Artificial
<220> FEATURE:
<223> OTHER INFORMATION: primer

<400> SEQUENCE: 55
cacccctaat acgactcact atagg 25

<210> SEQ ID NO 56
<211> LENGTH: 24
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (4)..(4)
<223> OTHER INFORMATION: n is a, c, g, or t

<400> SEQUENCE: 56
rttnccrtty tcrttytcyt craa 24

<210> SEQ ID NO 57
<211> LENGTH: 20
<212> TYPE: DNA
<213> ORGANISM: Artificial
<220> FEATURE:
<223> OTHER INFORMATION: primer

<400> SEQUENCE: 57
tgctgcaata tgaataccgc 20

<210> SEQ ID NO 58
<211> LENGTH: 24
<212> TYPE: DNA

-continued

```
<213> ORGANISM: Artificial
<220> FEATURE:
<223> OTHER INFORMATION: primer

<400> SEQUENCE: 58

gggcaggttt tttttttttt tttt                                    24
```